US010207004B2

(12) United States Patent
Baniel et al.

(10) Patent No.: US 10,207,004 B2
(45) Date of Patent: Feb. 19, 2019

(54) METHOD FOR PRODUCING SWEETENER COMPOSITIONS AND SWEETENER COMPOSITIONS

(71) Applicant: DouxMatok Ltd, Tel-Aviv (IL)

(72) Inventors: Avraham Baniel, Jerusalem (IL); Michael Zviely, Haifa (IL); Shay Eliyahu, Tel-Aviv (IL); Noa Gelbart, Herzliya (IL); Eran Baniel, Tel-Aviv (IL); Ronit Romm, Jerusalem (IL)

(73) Assignee: DouxMatok Ltd, Tel-Aviv (IL)

( * ) Notice: Subject to any disclaimer, the term of this patent is extended or adjusted under 35 U.S.C. 154(b) by 0 days.

(21) Appl. No.: 14/629,272

(22) Filed: Feb. 23, 2015

(65) Prior Publication Data

US 2015/0289550 A1    Oct. 15, 2015

Related U.S. Application Data

(60) Provisional application No. 61/975,683, filed on Apr. 4, 2014, provisional application No. 62/042,154, filed on Aug. 26, 2014, provisional application No. 62/074,518, filed on Nov. 3, 2014.

(51) Int. Cl.
| | | |
|---|---|---|
| *A61K 47/36* | (2006.01) |
| *A23L 27/30* | (2016.01) |
| *A23G 1/32* | (2006.01) |
| *A23G 1/40* | (2006.01) |
| *A23G 1/54* | (2006.01) |
| *A23G 3/36* | (2006.01) |
| *A23G 3/38* | (2006.01) |
| *A23G 3/42* | (2006.01) |
| *A23G 3/54* | (2006.01) |
| *A61K 9/16* | (2006.01) |

(52) U.S. Cl.
CPC ............... *A61K 47/36* (2013.01); *A23G 1/32* (2013.01); *A23G 1/40* (2013.01); *A23G 1/54* (2013.01); *A23G 3/36* (2013.01); *A23G 3/38* (2013.01); *A23G 3/42* (2013.01); *A23G 3/54* (2013.01); *A23L 27/30* (2016.08); *A23L 27/33* (2016.08); *A61K 9/1623* (2013.01)

(58) Field of Classification Search
CPC . A23L 1/22; A23L 27/30; A23L 27/33; A61K 47/26; A61K 47/28; A61K 9/1623; A61K 47/36; C07H 1/06; C07H 19/04; A23G 3/36; A23G 3/42; A23G 3/54; A23G 1/32; A23G 1/40
USPC ............ 127/30, 34, 36, 63; 426/96, 97, 238, 426/289, 495, 103
See application file for complete search history.

(56) References Cited

U.S. PATENT DOCUMENTS

| | | | |
|---|---|---|---|
| 3,175,299 A | * | 3/1965 | Boucher .................. A23L 3/54 127/15 |
| 3,503,803 A | * | 3/1970 | Bennett .................. C13B 30/022 127/16 |
| 3,988,162 A | | 10/1976 | Wason |
| 4,016,337 A | | 4/1977 | Hsu |
| 4,021,582 A | | 5/1977 | Hsu |
| 4,343,820 A | | 8/1982 | Roseman et al. |
| 4,513,012 A | | 4/1985 | Carroll et al. |
| 4,626,287 A | | 12/1986 | Shah et al. |
| 4,659,388 A | | 4/1987 | Innami et al. |
| 4,671,823 A | | 6/1987 | Shah et al. |
| 4,774,099 A | | 9/1988 | Feeney et al. |
| 4,925,693 A | | 5/1990 | Lauly |
| 4,976,972 A | | 12/1990 | Patel et al. |
| 4,981,698 A | | 1/1991 | Cherukuri et al. |
| 5,133,977 A | | 7/1992 | Patel |
| 5,145,707 A | | 9/1992 | Lee |
| 5,252,136 A | | 10/1993 | Desforges et al. |
| 5,260,091 A | | 11/1993 | Locke et al. |
| 5,266,335 A | | 11/1993 | Cherukuri et al. |
| 5,314,810 A | | 5/1994 | Kono et al. |
| 5,411,730 A | | 5/1995 | Kirpotin et al. |
| 5,492,814 A | | 2/1996 | Weissleder |
| 5,603,920 A | | 2/1997 | Rice |
| 5,651,958 A | | 7/1997 | Rice |
| 5,709,896 A | | 1/1998 | Hartigan et al. |
| 5,711,985 A | | 1/1998 | Guerrero et al. |
| 6,123,926 A | | 9/2000 | Parikh et al. |
| 6,248,378 B1 | | 6/2001 | Ganan-Calvo |
| 6,251,464 B1 | | 6/2001 | Felisaz et al. |
| 6,428,827 B1 | | 8/2002 | Song et al. |
| 6,461,658 B1 | | 10/2002 | Merkel et al. |
| 6,548,264 B1 | | 4/2003 | Tan et al. |
| 6,652,611 B1 | | 11/2003 | Huang et al. |
| 6,673,383 B2 | | 1/2004 | Cain et al. |

(Continued)

FOREIGN PATENT DOCUMENTS

| | | |
|---|---|---|
| AU | 2012202679 B2 | 3/2014 |
| CN | 2072973 U * | 3/1991 |

(Continued)

OTHER PUBLICATIONS

"International search report and written opinion dated Nov. 30, 2015 for PCT/IB2015/001153."
Co-pending U.S. Appl. No. 14/440,975, filed May 6, 2015.
Co-pending U.S. Appl. No. 14/677,715, filed Apr. 2, 2015.
U.S. Appl. No. 14/528,750, filed Oct. 30, 2014, Baniel.
Al-Ghouti, et al. New adsorbents based on microemulsion modified diatomite and activated carbon for removing organic and inorganic pollutants from waste lubricants. Chemical Engineering Journal vol. 173, Issue 1 Sep. 2011, 115-128.

(Continued)

*Primary Examiner* — Jyoti Chawla
(74) *Attorney, Agent, or Firm* — Wilson, Sonsini, Goodrich & Rosati

(57) ABSTRACT

Provided herein are compositions with enhanced sweetness or reduced caloric content per weight when compared to the sweetener carbohydrate or sweetener polyol component thereof, and methods for the preparation thereof.

19 Claims, 5 Drawing Sheets

(56) References Cited

U.S. PATENT DOCUMENTS

| | | |
|---|---|---|
| 6,703,057 B2 | 3/2004 | Duffett |
| 6,777,397 B2 | 8/2004 | Zehner et al. |
| 7,118,765 B2 | 10/2006 | Norman et al. |
| 7,122,215 B2 | 10/2006 | Ludwig et al. |
| 7,163,708 B2 | 1/2007 | Dalziel et al. |
| 7,258,885 B2 | 8/2007 | Seltzer et al. |
| 7,267,835 B2 | 9/2007 | Kitazume et al. |
| 7,282,217 B1 | 10/2007 | Grimshaw et al. |
| 7,544,379 B2 | 6/2009 | Kawamura et al. |
| 7,744,922 B2 | 6/2010 | Mane et al. |
| 7,754,239 B2 | 7/2010 | Mane et al. |
| 7,763,570 B1 | 7/2010 | Rayborn, Sr. et al. |
| 7,815,936 B2 | 10/2010 | Hasenzahl et al. |
| 7,838,033 B2 | 11/2010 | Tanaka et al. |
| 7,838,055 B2 | 11/2010 | Eroma et al. |
| 7,842,324 B2 | 11/2010 | Tachdjian et al. |
| 7,851,005 B2 | 12/2010 | Hargreaves et al. |
| 7,851,006 B2 | 12/2010 | Bingley et al. |
| 7,879,376 B2 | 2/2011 | Boghani et al. |
| 7,955,630 B2 | 6/2011 | Boghani et al. |
| 7,972,995 B2 | 7/2011 | Rayborn, Sr. et al. |
| 8,119,173 B2 | 2/2012 | Cheng et al. |
| 8,192,775 B2 | 6/2012 | Eroma et al. |
| 8,216,981 B2 | 7/2012 | Rayborn, Sr. et al. |
| 8,349,361 B2 | 1/2013 | Tanaka et al. |
| 8,545,889 B2 | 10/2013 | Norman et al. |
| 8,617,588 B2 | 12/2013 | Tillotson et al. |
| 8,647,668 B2 | 2/2014 | Tanaka et al. |
| 8,663,682 B2 | 3/2014 | Chenevier et al. |
| 8,673,825 B2 | 3/2014 | Rayborn, Sr. et al. |
| 8,697,167 B2 | 4/2014 | Stouffs et al. |
| 8,911,806 B2 | 12/2014 | Baniel |
| 8,962,058 B2 | 2/2015 | Prakash et al. |
| 9,023,418 B2 | 5/2015 | Baniel |
| 9,028,906 B2 | 5/2015 | Baniel |
| 9,144,251 B2 | 9/2015 | Prakash et al. |
| 9,271,942 B2 | 3/2016 | Ramtoola |
| 9,358,212 B2 | 6/2016 | Tillotson et al. |
| 9,446,055 B2 | 9/2016 | Fujiwara et al. |
| 9,668,504 B2 | 6/2017 | Baniel et al. |
| 2001/0004869 A1 | 6/2001 | Cantiani et al. |
| 2001/0055572 A1 | 12/2001 | Thomas et al. |
| 2003/0014014 A1 | 1/2003 | Nitzan |
| 2003/0039617 A1 | 2/2003 | White et al. |
| 2003/0129227 A1 | 7/2003 | Yamaguchi |
| 2004/0068224 A1 | 4/2004 | Couvillon, Jr. et al. |
| 2004/0161498 A1 | 8/2004 | Barrero et al. |
| 2005/0130240 A1 | 6/2005 | Chun-Cheng et al. |
| 2005/0244568 A1 | 11/2005 | Gokhan |
| 2006/0024335 A1 | 2/2006 | Roger |
| 2006/0073255 A1 | 4/2006 | Catani et al. |
| 2006/0102455 A1 | 5/2006 | Chiang et al. |
| 2007/0003680 A1 | 1/2007 | Tachdjian et al. |
| 2007/0116827 A1 | 5/2007 | Prakash et al. |
| 2007/0116832 A1 | 5/2007 | Prakash et al. |
| 2008/0044521 A1 | 2/2008 | Eddies et al. |
| 2008/0193531 A1 | 8/2008 | Hermelin et al. |
| 2008/0213452 A1 | 9/2008 | Miles et al. |
| 2008/0292765 A1 | 11/2008 | Prakash et al. |
| 2008/0311398 A1 | 12/2008 | Bauer et al. |
| 2009/0053378 A1 | 2/2009 | Prakash et al. |
| 2009/0297670 A1 | 12/2009 | Baniel |
| 2010/0129516 A1 | 5/2010 | Siegel |
| 2011/0027355 A1 | 2/2011 | Lefevre et al. |
| 2011/0027444 A1 | 2/2011 | Gelov |
| 2011/0052755 A1 | 3/2011 | Fiorenza et al. |
| 2011/0059218 A1 | 3/2011 | Corliss et al. |
| 2011/0064861 A1 | 3/2011 | Shimono et al. |
| 2012/0088025 A1 | 4/2012 | Baniel et al. |
| 2012/0207890 A1 | 8/2012 | Johal et al. |
| 2013/0236604 A1 | 9/2013 | De |
| 2013/0273165 A1 | 10/2013 | Buchner |
| 2014/0010939 A1 | 1/2014 | Krohn et al. |
| 2014/0271747 A1 | 9/2014 | Woodyer et al. |
| 2015/0047630 A1 | 1/2015 | Baniel |
| 2015/0189904 A1 | 7/2015 | Prakash et al. |
| 2015/0275319 A1 | 10/2015 | Baniel |
| 2016/0045518 A1 | 2/2016 | Dohil et al. |
| 2016/0242439 A1 | 8/2016 | Baniel et al. |
| 2016/0331012 A1 | 11/2016 | Baniel et al. |
| 2017/0215461 A1 | 8/2017 | Baniel et al. |

FOREIGN PATENT DOCUMENTS

| | | |
|---|---|---|
| CN | 103504256 A | 1/2014 |
| EP | 0427541 A2 | 5/1991 |
| EP | 1447074 A2 | 8/2004 |
| FR | 2808657 B1 | 6/2003 |
| GB | 721605 A | 1/1955 |
| GB | 2025227 A | 1/1980 |
| HK | 1158629 A1 | 10/2015 |
| IL | 169678 A | 11/2010 |
| IL | 180687 A | 4/2011 |
| IL | 180687 A | 4/2011 |
| JP | 4364122 A | 12/1992 |
| JP | 2001352936 A | 12/2001 |
| NZ | 556774 A | 2/2011 |
| WO | WO-9012117 A2 | 10/1990 |
| WO | WO-9414330 A1 | 7/1994 |
| WO | WO-9416576 A1 | 8/1994 |
| WO | WO 99/20127 A1 | 4/1999 |
| WO | WO 01/13740 A1 | 3/2001 |
| WO | WO-02051391 A2 | 7/2002 |
| WO | WO-02096213 A1 | 12/2002 |
| WO | WO-03045166 A1 | 6/2003 |
| WO | WO-2004005227 A1 | 1/2004 |
| WO | WO-2004066974 A1 | 8/2004 |
| WO | WO-2004089113 A1 | 10/2004 |
| WO | WO 2004/098555 A1 | 11/2004 |
| WO | WO-2005037254 A1 | 4/2005 |
| WO | WO-2005037849 A1 | 4/2005 |
| WO | WO 2005/084457 A1 | 9/2005 |
| WO | WO 2006/015880 A1 | 2/2006 |
| WO | WO-2006012763 A1 | 2/2006 |
| WO | WO 2006/062089 A1 | 6/2006 |
| WO | WO-2006072921 A2 | 7/2006 |
| WO | WO 2007/007310 A1 | 1/2007 |
| WO | WO 2007/061810 A2 | 5/2007 |
| WO | WO-2007061757 A1 | 5/2007 |
| WO | WO-2007061858 A1 | 5/2007 |
| WO | WO-2007061900 A1 | 5/2007 |
| WO | WO-2007061912 A2 | 5/2007 |
| WO | WO-2007081442 A2 | 7/2007 |
| WO | WO-2008042417 A1 | 4/2008 |
| WO | WO 2009/006208 A2 | 1/2009 |
| WO | WO 2009/087215 A2 | 7/2009 |
| WO | WO-2009151072 A1 | 12/2009 |
| WO | WO 2010/025158 A1 | 3/2010 |
| WO | WO-2011019045 A1 | 2/2011 |
| WO | WO-2013045318 A1 | 4/2013 |
| WO | WO-2013082019 A1 | 6/2013 |
| WO | WO-2015015210 A1 | 2/2015 |
| WO | WO-2015150915 A2 | 10/2015 |
| WO | WO-2015159156 A2 | 10/2015 |
| WO | WO-2017037531 A2 | 3/2017 |
| WO | WO-2017037531 A3 | 4/2017 |

OTHER PUBLICATIONS

Fennema, Food Chemistry Third Edition 1996, Marcel Drekker Publication, Pertinent p. 193.

Graneinetti Laboratory (undated) http://www.grandinetti.org/Teaching/Chem121/Lectures/VSEPR.

Handbuch Subungsmittel: Eigenschaften and Anwendung. pp. 162-165. G.W. von Rymon Lipinski and H. Hamburg, Germany (1990). ISBN: 3-925673-77-6 (in German).

International search report and written opinion dated Apr. 4, 2014 for PCT Application No. IL2013/050851.

International search report and written opinion dated Jul. 20, 2006 for PCT Application No. IL2006/00573.

Kelly, et al. Phase Equilibria in the System Sucrose-Glucose-Fructose. J. appl. Chem. May 4, 1967. 17.5: 125-126.

Middle School Chemistry (undated) http://www.middleschoolchemistry.com/multimedia/chapter4/lesson6.

(56) References Cited

OTHER PUBLICATIONS

Notice of Allowance dated Jan. 2, 0215 for U.S. Appl. No. 13/250,088.
Notice of allowance dated Feb. 13, 2015 for U.S. Appl. No. 14/511,046.
Notice of allowance dated Oct. 6, 2014 for U.S. Appl. No. 11/995,464.
Office action dated Jan. 7, 2013 for U.S. Appl. No. 13/250,088.
Office action dated Jan. 10, 2013 for U.S. Appl. No. 11/995,464.
Office action dated Jan. 10, 2014 for U.S. Appl. No. 11/995,464.
Office action dated Apr. 18, 2012 for U.S. Appl. No. 11/995,464.
Office action dated May 30, 2013 for U.S. Appl. No. 13/250,088.
Office action dated Jul. 30, 2014 for U.S. Appl. No. 13/250,088.
Office action dated Aug. 15, 2011 for U.S. Appl. No. 11/995,464.
Office action dated Sep. 10, 2014 for U.S. Appl. No. 13/250,088.
Pending claims dated May 15, 2014 for U.S. Appl. No. 13/250,088.
Pending claims dated Aug. 28, 2014 for U.S. Appl. No. 13/250,088.
Smith, Jim; Hong-Shum, Lily (2003). Food Additives Data Book. (pp. 704-707). Blackwell Publishing. Online version available at: http://www.knovel.com/web/portal/browse/display?_EXT_KNOVEL_DISPLAY_bookid=1381&VerticalID=0.
The surface chemistry of amorphous silica. Zhuravlev model L.T. Zhuravlev Institute of Physical Chemistry, Russian Academy of Sciences, Leninsky Prospect 31, Moscow 117915, Russia Feb. 2000 Elsevier, 38 pages.
Co-pending U.S. Appl. No. 15/045,145, filed Feb. 16, 2016.
International search report and written opinion dated Jan. 7, 2016 for PCT Application No. PCT-IB15-00773.
Office action dated Mar. 28, 2016 for U.S. Appl. No. 14/440,975.
Co-pending U.S. Appl. No. 15/756,040, filed Feb. 27, 2018.
Co-pending U.S. Appl. No. 15/756,042, filed Feb. 27, 2018.
Narducci, Olga. Particle Engineering via Sonocrystallization: The Aqueous Adipic Acid System. University College of London: Department of Chemical Engineering. p. 65 of Ph.D. Thesis. Oct. 2012. 2 pages.
Bergna, Horacio E, Ed. The Colloidal Chemistry of Silica, ACS Publications, p. 21-30, 341-353, 1994.
European search report and search opinion dated Oct. 27, 2017 for European Patent Application No. 15780074.9.
Hafiz, et al. Synthesis of quality silica gel; Optimization of parameters. Journal of Faculty of Engineering & Technology, 2009, 14 pages.

Kinrade, et al. Aqueous hypervalent silicon complexes with aliphatic sugar acids. J. Chem. Soc., Dalton Trans., 2001,0, 961-963.
Kinrade, et al. Silicon-29 NMR evidence of alkoxy substituted aqueous silicate anions. J. Chem. Soc., Dalton Trans., 1999, 3149-3150.
Kinrade, et al. Stable five- and six-coordinated silicate anions in aqueous solution. Science. Sep. 3, 1999;285(5433):1542-5.
Martin, K.R. The Chemistry of Silica and Its Potential Health Benefits. The Journal of Nutrition, Health & Aging; Paris vol. 11(2), (Mar./Apr. 2007): 94-7.
Office action dated Sep. 18, 2017 for U.S. Appl. No. 15/487,274.
Office action dated Oct. 6, 2017 for U.S. Appl. No. 15/222,916.
Rombauer, I. S., Rombauer Becker, M., Becker, E. 1997. Joy of Cooking. Scribner: New York. p. 1010.
Storer, Ian. Hypervalent Silicon: Bonding, Properties and Synthetic Utility, MacMillan Group Meeting, Jul. 20, 2005.
International Search Report and Written Opinion dated Feb. 16, 2017 for PCT Application No. PCT/IB2016/01284.
International Search Report and Written Opinion dated Feb. 9, 2017 for PCT Application No. PCT/IB2016/01322.
Notice of allowance dated Mar. 22, 2017 for U.S. Appl. No. 14/528,750.
Office action dated Nov. 18, 2016 for U.S. Appl. No. 14/528,750.
Co-pending U.S. Appl. No. 15/489,696, filed Apr. 17, 2017.
"International search report with written opinion dated Dec. 12, 2016 for PCT/IB2016/00818".
Office action dated Apr. 27, 2017 for U.S. Appl. No. 15/222,916.
"Tamura M, et al. An enhancing effect on the saltiness of sodium chloride of added amino acids and their esters. Agricultural and Biological Chemistry. 1989, vol. 53, No. 6, pp. 1625-1633".
U.S. Appl. No. 14/528,750 Office Action dated May 9, 2016.
U.S. Appl. No. 15/045,145 Office Action dated Aug. 15, 2016.
Lionnet, et al. Aspects of the Effects of Silica During Cane Sugar Processing. Proc S Afr Sug Technol Ass. vol. 78. 2004, 55-64.
Madho, et al. Silica in low grade refinery sugar Proc S Afr Sug Technol Ass. vol. 84. 2011, 516-527.
U.S. Appl. No. 15/487,274 Notice of Allowance dated Nov. 9, 2018.
U.S. Appl. No. 15/222,916 Notice of Allowance dated Oct. 25, 2018.
U.S. Appl. No. 15/489,696 Notice of Allowance dated Dec. 12, 2018.

* cited by examiner

METHOD FOR PRODUCING SWEETENER COMPOSITIONS AND SWEETENER COMPOSITIONS

CROSS-REFERENCE

This application claims priority from U.S. Provisional Application No. 61/975,683, filed Apr. 4, 2014; U.S. Provisional Application No. 62/042,154, filed Aug. 26, 2014; and U.S. Provisional Application No. 62/074,518, filed Nov. 3, 2014; each of which is hereby incorporated by reference in its entirety.

FIELD OF THE INVENTION

The present disclosure relates to sweetener compositions. More particularly, the present invention relates to carbohydrate sweetener compositions and polyol sweetener compositions having enhanced sweetness and reduced caloric content as compared to that of the carbohydrate component or polyol component thereof, and to methods for the preparation thereof.

BACKGROUND OF THE INVENTION

Certain carbohydrates and polyols are commonly used as sweeteners. Sucrose, glucose, and other many sweet monosaccharides, di-saccharides, and other oligosaccharides are fully metabolized when consumed in food. Thus, for each natural carbohydrate sweetener the provision of sweetness correlates with the provision of calories in a rigidly fixed proportion. Excess sugar intake can post several health problems. Artificial sweeteners have been used for years to reduce dietary sugar content, but they are not ideal substitutes for sugar owing to their after taste, absence of energy provided by sugars and some health concerns. Sweetener polyols can offer a reduced calorie load and varying sweetness as compared to sweetener carbohydrates, however the cost of some sweetener polyols can be high. In such cases, a method to increase the sweetness of sweetener carbohydrates or sweetener polyols or reduce the amount of sweetener carbohydrates or sweetener polyols to achieve equivalent sweetness is desired. Another strategy emerging is focused on allosteric modulation of the sweet taste receptor by sweet taste enhancers. These molecules do not taste sweet, but can significantly potentiate the perception of the sweet taste of sucrose and other sweeteners selectively, however can be limited in both strength and selectivity. The present disclosure provides for the manipulation of the proportion between sweetener amount and calories so that a desired sweetness may correlate with lower calorie values. This is achieved through the presentation of the carbohydrate sweetener or polyol sweetener in the form of a composition belonging to a class of compositions described below. Differently put, the perception of sweetness of a sweetener carbohydrate or sweetener polyol is retained while reducing the caloric value thereof by virtue of it being provided in a composition as described hereinafter.

SUMMARY OF THE INVENTION

Provided herein is a method of making a sweetener composition, comprising mechanically coating a carrier compound with one or more sweetener carbohydrates or sweetener polyols; wherein the sweetener composition has enhanced sweetness compared to a control composition; and wherein the control composition consists of the same contents by identity and quantity as the sweetener composition but without the carrier compound. In some embodiments, the method comprises sonicating the sweetener composition to form a sonicated sweetener composition. In some embodiments, the method comprises passing the sweetener composition through a sieve or sieving tower to remove particles of particular sizes and to form a selectively sieved sweetener composition. In some embodiments, the mechanical coating is by mortar and pestle or mechanical grinder. In some embodiments, the sweetness is enhanced by at least 10, 20, 30, 40 or 50%, for example, the sweetness is enhanced by 40-60%.

Further provided herein is an isolated sweetener composition comprising: at least one sweetener carbohydrate or sweetener polyol; and 6-12% carrier compound weight/weight (wt/wt) relative to a sum of total sweetener carbohydrate and sweetener polyol; wherein the sweetener composition has enhanced sweetness compared to a control composition; and wherein the control composition consists of comparable contents to the sweetener composition, but lacks the carrier compound. In some embodiments, the compositions comprises about 8-10% carrier compound wt/wt relative to a sum of total sweetener carbohydrate and sweetener polyol, for example, 8% carrier compound wt/wt relative to a sum of total sweetener carbohydrate and sweetener polyol. In some embodiments, the at least one sweetener carbohydrate is high fructose corn syrup. In some embodiments, the at least one sweetener carbohydrate is high maltose corn syrup. In some embodiments, each of the at least one sweetener carbohydrates is selected from the group consisting of sucrose and glucose. In some embodiments, the at least one sweetener carbohydrate is sucrose, glucose, maltose, lactose, high fructose corn syrup, high maltose corn syrup, or a combination thereof. In some embodiments, the at least one sweetener carbohydrate is not fructose. In some embodiments, the composition comprises a sweetener polyol. In some embodiments, the sweetener polyol is selected from the group consisting of xylitol, maltitol, erythritol, and sorbitol. In some embodiments, the sweetener polyol is xylitol, maltitol, erythritol, sorbitol, threitol, arabitol, hydrogenated starch hydrolysates (HSH), isomalt, lactitol, mannitol, galactitol (dulcitol), or a combination thereof. In some embodiments, the composition comprises at least one sweetener carbohydrate, at least one sweetener polyol, or a combination thereof.

In some embodiments, the carrier compound is chitosan. In some embodiments, the carrier compound is silica. In some embodiments, the carrier compound is precipitated silica. In some embodiments, the carrier compound is porous silica. In some embodiments, the carrier compound is porous, precipitated silica. In some embodiments, the carrier compound is silica gel. In some embodiments, the carrier compound is amorphous silica. In some embodiments, the carrier compound is precipitated, amorphous silica. In some embodiments, the carrier compound is Perkasil® (W. R. Grace & Co). In some embodiments, the carrier compound is Perkasil® SM 660 (W. R. Grace & Co). In some embodiments, the carrier compound is SYLOID® (W. R. Grace & Co). In some embodiments, the carrier compound is SYLOX® (W. R. Grace & Co). In some embodiments, the carrier compound is Tixosil® (Solvay). In some embodiments, the carrier compound is Tixosil® 38AB (Solvay). In some embodiments, the carrier compound contains a moisture level or water content of 0 to 6% by weight (wt). In some embodiments, the composition is comprised of at least 10%, 20%, 30%, 40%, 50%, 60%, 70%, 80%, 90%, or 95% sweetener carbohydrate and carrier compound by weight. In some embodiments, the composition consists essentially of sweetener carbohydrate and carrier compound. In some embodiments, the composition consists of sweetener carbohydrate and carrier compound. In some embodiments, the composition is comprised of at least 50%, 60%, 70%, 80%, 90%, or 95% sweetener polyol and carrier compound by weight. In some embodiments, the composition consists essentially of sweetener polyol and carrier compound. In some embodiments, the composition consists of sweetener polyol and carrier compound. In some embodiments, the composition is comprised of at least 10%, 20%, 30%, 40%, 50%, 60%, 70%, 80%, 90%, or 95% sweetener carbohydrate, sweetener polyol, and carrier compound by weight. In some embodiments, the composition consists essentially of sweetener carbohydrate, sweetener polyol, and carrier compound. In some embodiments, the composition consists of sweetener carbohydrate, sweetener polyol, and carrier compound. In some embodiments, the composition does not comprise DNA, protein, lignin, or magnetic particles. In some embodiments, the composition reduces the perceived bitterness of a food or a consumable product.

Further provided herein is a composition comprising a food or a consumable product comprising the sweetener composition provided herein. In some embodiments, the food or consumable product is selected from the group consisting of confectionary, chocolate, baked goods, condiments, sauces, dressings, tooth paste, chewing gum, pharmaceutical syrups, and dairy products. In some embodiments, the food or consumable product is less bitter than a control product, wherein the control product is identical to the food or consumable product but lacks the sweetener composition described herein. In some embodiments, the food or consumable product contains up to 0.1, 0.5, 1.0, 1.1, 1.2, 1.3, 1.4, 1.5, 1.6, 1.7, 1.8, 1.9, or 2.0% silica wt/wt.

Also provided herein is a syrup sweetener composition comprising at least one sweetener carbohydrate or sweetener polyol and 6-12% carrier compound wt/wt relative to a sum of total sweetener carbohydrate and sweetener polyol; wherein the sweetener composition has enhanced sweetness compared to a control composition; and wherein the control composition consists of comparable contents to the sweetener composition but lacks the carrier compound. In some embodiments, the syrup comprises 8-10% carrier compound wt/wt relative to a sum of total sweetener carbohydrate and sweetener polyol.

Additionally provided herein is a method to make a food or consumable product comprising substituting at least a portion of a sweetener ingredient with the sweetener composition described herein.

Figure 1:
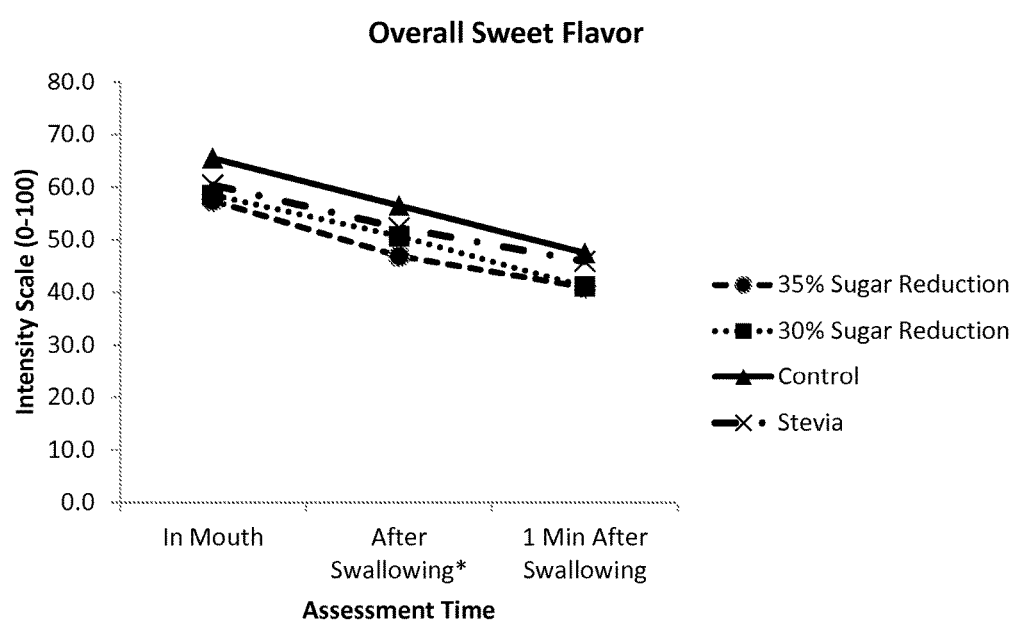
FIG. 1 shows overall sweet flavor intensity as a function of time for whipped double cream samples.

The novel features of the invention are set forth with particularity in the appended claims. A better understanding of the features and advantages of the present invention will be obtained by reference to the following detailed description that sets forth illustrative embodiments, in which the principles of the invention are utilized.

DETAILED DESCRIPTION OF THE INVENTION

Components of Sweetener Compositions

The present disclosure relates to sweetener compositions that can be used alone or be added to, or further processed into a food or a consumable product. The sweetener compositions herein comprise at least one sweetener carbohydrate or sweetener polyol.

As used herein, the term "sweetener carbohydrate" refers to a consumable carbohydrate which produces a sweet taste when consumed alone. In some cases, a sweetener carbohydrate is a monosaccharide or disaccharide. A sweetener carbohydrate can be sucrose, glucose, maltose, lactose, high fructose corn syrup, high maltose corn syrup, or a combination thereof. A sweetener carbohydrate can be sucrose, glucose, maltose, lactose, or a combination thereof. A sweetener carbohydrate can be high fructose corn syrup or high maltose corn syrup, or a combination thereof. A sweetener carbohydrate can be a naturally-occurring carbohydrate. For example, it may be an isolated, purified sweetener. A sweetener carbohydrate can also be a non-naturally occurring, synthetically-produced carbohydrate.

As used herein, the term "sweetener polyol" refers to a consumable polyol which produces a sweet taste when consumed alone. Some non-limiting examples of sweetener polyols include xylitol, maltitol, erythritol, sorbitol, threitol, arabitol, hydrogenated starch hydrolysates (HSH), isomalt, lactitol, mannitol, galactitol (dulcitol). In some instances, the polyol is a sugar alcohol. A sugar alcohol can be produced from a corresponding parent carbohydrate by any known method of reduction (via a chemical or biological transformation) of an acid or aldehyde to an alcohol. In some cases, a sweetener polyol can be created synthetically from a parent carbohydrate. Alternatively or in combination, a sweetener polyol can be bio-derived or obtained from a biological source.

As used herein, the term "about" can be understood as within 10%, 9%, 8%, 7%, 6%, 5%, 4%, 3%, 2%, 1%, 0.5%, 0.1%, 0.05%, or 0.01% of the stated value.

In some sweetener compositions described herein, the composition comprises one or more sweetener polyols. In some cases, a sweetener polyol can be covalently attached to a carbohydrate (e.g. a monosaccharide, or di-saccharide). In some cases, a sweetener composition comprises one or more sweetener polyols selected from the group consisting of xylitol, maltitol, erythritol, sorbitol, threitol, arabitol, hydrogenated starch hydrolysates (HSH), isomalt, lactitol, mannitol, galactitol (dulcitol).

As used herein, the term "carrier compound" refers to a solid, food-grade material which can be coated with a sweetener. A carrier compound through its large and active surface and structure forms hydrogen bonds with the sweetener carbohydrate and/or sweetener polyol. As such, the carbohydrate and/or polyol can maintain its chemical integrity. For instance, the interaction between the carrier compound and the carbohydrate and/or polyol does not need to involve covalent bonds. In some embodiments, the carrier compound associates with the sweetener carbohydrate and/or sweetener polyol to provide characteristics different than a control composition, for instance enhanced sweetness, reduced bitterness, or reduced rate of dissolution; wherein the control composition consists of the same contents by identity and quantity as the sweetener composition but without the carrier compound. In some embodiments, a carrier compound is non-hygroscopic. In some embodiments, a carrier compound is relatively inexpensive and can be obtained or produced in large quantities. A carrier compound can be a solid composition lacking a distinctive taste. In some embodiments, a carrier compound is flavorless and odorless. In some cases, digestion of a carrier compound by a human produces a low amount of usable calories. In some cases, a carrier compound is non-caloric. Some non-limiting examples of a carrier compound are silica, silicon dioxide, chitosan, chitin, starch, maltodextrin, microcrystalline cellulose, hemicellulose, cyclodextrins, hydroxyalkyl cyclodextrins (e.g., hydroxypropyl and methyl cyclodextrins), inulin, pectin, carrageenans, titanium dioxide, magnesium oxide, magnesium hydroxide, calcium oxide, calcium carbonate, and natural gums (e.g., gum arabic, gellan gum, guar gum, locust bean gum, and xanthan gum). In some embodiments, a carrier compound is a combination of more than one distinct carrier compounds. In some embodiments, a solid carrier compound can be at least partially dissolved in a solvent (e.g., water).

In some embodiments, a carrier compound comprises silica or silicon dioxide ($SiO_2$). A carrier compound optionally meets the test requirements for silicon dioxide as described in the Food Chemicals Codex (FCC), the European Directive, or Japan's Specifications and Standards for Food Additives. In some embodiments, a carrier compound is colloidal silica or silica particles. In some embodiments, a carrier compound is precipitated silica. In some embodiments, silica particles are particles comprising silica. In some embodiments, silica particles are particles consisting essentially of silica. In some embodiments, silica particles are particles consisting of silica. A carrier compound can have an average particle size up to 10, 20, 30, 40, 50, 60, 70, 80, 90, or 100 microns. In some embodiments, a carrier compound can have an average particle size of at least 1, 2, 3, 4, 5, 7, 8, 9, 10, 11, 12, 13, 14, 15, 20, 25, 30, 35, 40, 45, 50, or 100 microns. In some embodiments, a carrier compound has an average particle size between 5 and 100, 10 and 80, 10 and 50, or 10 and 30 microns.

In some embodiments, a carrier compound can have a high specific surface area. In some embodiments, a carrier compound can have a specific surface area higher than 20, 30, 40, 50, 60, 70, 80, 90, 100, 110, 120, 130, 140, 150, 160, 170, 180, 190, 200, or 210 $m^2/g$, for example. In some embodiments, a carrier compound can have a specific surface area between 150 and 300 $m^2/g$ or between 170 and 210 $m^2/g$.

In some embodiments, a carrier compound is in a dehydrated state. For example, the decrease in mass upon drying of a carrier compound can be up to 1, 2, 3, 4, 5, 6, 7, 8, 9, or 10%. In some cases, a carrier compound can be annealed before being coated with one or more sweetener carbohydrates and/or sweetener polyols. In some cases, a carrier compound can be dried before being coated with one or more sweetener carbohydrates and/or sweetener polyols. In some cases, a carrier compound have moisture or water added to it before being coated with one or more sweetener carbohydrates and/or sweetener polyols. In some cases, a carrier compound can contain a moisture level or water content of 0-6%, 0-5%, 1-6%, 1-5%, 2-6%, 1-4%, 2-5%, 3-6%, 1-3%, 2-4%, 3-5%, or 4-6% wt/wt before being coated with one or more sweetener carbohydrates and/or sweetener polyols. In some cases, a carrier compound can contain up to 0.01%, 0.05%, 0.1%, 0.5%, 1%, 1.5%, 2%, 2.5%, 3%, 3.5%, 4%, 4.5%, 5%, 5.5%, or 6% water wt/wt before being coated with one or more sweetener carbohydrates and/or sweetener polyols. In some cases, a carrier can be heated (e.g., at 400° C.) for at least 0.5, 1, 1.5, 2, 2.5, 3, 3.5, or 4 hours to remove moisture and dry the carrier.

Methods of Making Sweetener Compositions

The sweetener compositions herein can be manufactured, e.g. using the methods below. A carrier compound can be coated with one or more sweetener carbohydrates and/or sweetener polyols to produce a sweetener composition with enhanced sweetness. A carrier compound can be coated with and one or more sweetener carbohydrates and/or sweetener polyols by one or more mechanical methods. Non limiting examples of mechanical coating methods include stirring, grinding, compressing, blending, agitating, rotational mixing, solid-solid mixing with a static mixer, Kenics mixing, drum tumbling, and Turbula mixing, for example. In some cases, two or more forms of mechanical methods can be used in series or in parallel. For example, in some cases, one or more sweetener carbohydrates and/or sweetener polyols and one or more carrier compounds can be mixed together, ground mechanically in a grinder, and subsequently further ground mechanically via mortar and pestle to achieve coating of the carrier.

In some cases, a carrier compound can be coated with one or more sweetener carbohydrates and/or sweetener polyols by preparing a dry formulation without using water. For example, one or more sweetener carbohydrates and/or sweetener polyols and a carrier compound can be mixed to form a powder and then subsequently ground together to form hydrogen bonds between the sweetener coating and the carrier compound. In some cases, the dry grinding can form a substantially homogenous solid powder mixture.

The conditions of the mechanical coating or grinding (e.g., temperature, time duration, speed, timing, rate, force, pressure, etc.) can affect the sweetness of the resulting composition. In some cases, these conditions are selected to give the largest enhancement of sweetness to the resulting composition. In some cases, grinding is carried out for up to 0.1, 0.2, 0.3, 0.4, 0.5, 1.0, 2.0, 3.0, 4.0, 5.0, 6.0, 7.0, 8.0, 9.0, 10.0, 12.0, 14.0, 16.0, 18.0, or 20.0 min. In some cases, the grinding can be carried out for at least 0.1, 0.2, 0.3, 0.4, 0.5, 1.0, 2.0, 3.0, 4.0, 5.0, 6.0, 7.0, 8.0, 9.0, 10.0, 12.0, 14.0, 16.0, 18.0, or 20.0 min. In some cases when two or more forms of mechanical methods are used in series or in parallel, the timing and conditions of each form can be selected independently.

In some cases, a method to formulate a sweetener composition comprising one or more sweetener carbohydrates and/or sweetener polyols and one or more carrier compounds can comprise sieving or sonicating the carrier compound coated with one or more sweetener carbohydrates and/or sweetener polyols. A sweetener composition as described herein can be sieved, or passed through a sieve or sieving tower to remove particles of at least a minimum size, of at most a maximum size, or of at least a minimum size and of at most a maximum size from the composition. In some cases, the sieve can have a mesh with openings up to 30, 40, 50, 60, 70, 80, 90, 100, 110, 120, 130, 140, 150, 160, 170, 180, 190, or 200 mesh. In some cases, the sieve can have a have mesh with openings of about 40 to about 100 mesh. In some cases, the sieve can have a mesh from about 60 to about 70. In some cases, the solid mixture can be subjected to sonication. The sonication can be for at least 1, 2, 3, 4, 5, 6, 7, 8, 9, 10, 12, 14, 16, 20, 24, 30, 40, 50, or 60 min. In some cases, the sonication occurs while the mixture is heated to at least 30, 35, 40, or 45° C. In some cases the sonication occurs during the grinding or during the mixing. In some cases, the composition is not sonicated.

In some cases, a method of producing a sweetener composition comprises mixing one or more sweetener carbohydrates and/or sweetener polyols and a carrier compound without adding water, grinding the mixture of solids in a mechanical grinder, grinding the mixture in a mortar and pestle, passing the composition through a sieve with a mesh having an opening between about 40 and about 100 mesh, and subsequently sonicating the mixture for at least 5 min.

A carrier compound and one or more sweetener carbohydrates can be mixed by using a solvent or volatile liquid. For example, a carrier compound and one or more sweetener carbohydrates and/or sweetener polyols can be mixed by using a solvent or volatile liquid to form a paste that can be dried to obtain a solid. In some embodiments, a carrier compound and one or more sweetener carbohydrates and/or sweetener polyols can be mixed by using a solvent or volatile liquid to form a substantially uniform paste that can be dried to obtain a substantially uniform solid. In some embodiments, the solvent or volatile liquid can be water or iso-propanol for example.

In some cases, a syrup can be formed by mixing one or more sweeteners with water, and a carrier compound can be added to the syrup. In some cases, a syrup can be formed by mixing one or more sweetener carbohydrates and/or sweetener polyols with water, and a carrier compound can be added to the syrup. Alternatively or in combination, the carrier compound can be added to the water prior to the addition of the sweetener. Alternatively or in combination, the carrier compound and the one or more sweetener carbohydrates and/or sweetener polyols can be mixed together prior to being added to the water. In some cases, a sweetener composition can comprise a syrup comprising water one or more sweetener carbohydrates and/or sweetener polyols, and a carrier compound. In some cases, a sweetener composition can comprise a syrup comprising 6-12% carrier compound wt/wt relative to a sum of total sweetener carbohydrate and/or sweetener polyol. In some cases, a sweetener composition can comprise a syrup comprising water and one or more sweetener carbohydrates and/or sweetener polyols in a ratio of total sweetener carbohydrate and/or sweetener polyol to water of at least 55:45, 60:40, or 65:35. In some cases, a method to form a sweetener composition comprises mixing one or more sweetener carbohydrates (i.e. sucrose) and/or sweetener polyols with water at 70° C. in a ratio of 65/35 carbohydrate/water wt/wt, slowly adding a carrier compound (i.e. silica) up to 8% wt/wt relative to the sum of sweetener carbohydrates (i.e. sucrose) and/or sweetener polyols to form a syrup of sweetener coated carrier, and sonicating the syrup. In some cases, the syrup or its individual components can be subjected to sonication. The sonication can be for at least 1, 2, 3, 4, 5, 6, 7, 8, 9, 10, 12, 14, 16, 20, 24, 30, 40, 50, or 60 min. In some cases, the sonication occurs while the mixture is heated. In some cases the sonication occurs during the mixing. In some cases, the composition is not sonicated. The syrup sweetener composition can be used for many applications described herein. Alternatively or in combination, the syrup sweetener composition can be dried to form a dry solid sweetener composition.

The paste or syrup resulting from the use of a solvent or a volatile liquid can be dried via any standard drying method to form a dry solid sweetener composition. Some non-limiting examples of drying methods include, thermal drying, evaporation, heating in an oven, vacuum drying, spray drying, freeze-drying, lyophilization, or a combination thereof. The mechanism of drying can affect the hydration and molecular structure of the composition thus giving rise to sweetener compositions with different physical properties. For example, in some cases, the paste or syrup is dried in the oven (e.g. 12-80 hours, at 60° C.) until a solid dehydrated sweetener product remains. The paste or syrup can be dried until the composition comprises up to 0.001, 0.005, 0.01, 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0, 10.0, 11.0, 12.0, 13.0, 14.0, 15.0, 16.0, 17.0, 18.0, 19.0, or 20.0% water wt/wt.

Ratios of Sweetener Composition Components

A sweetener composition comprising a carrier compound and one or more sweeteners can have a defined ratio of amounts of the carrier compound and the one or more sweeteners. The ratio of amounts of a carrier compound to one or more sweetener carbohydrates and/or sweetener polyols can be determined by weight, volume, mole, or a combination thereof. In some embodiments, a sweetener composition can comprise a carrier compound and one or more sweeteners in a ratio (weight/weight) of at least 6, 7, 8, 9, 10, 11, or 12 parts carrier compound to 100 parts total sweetener. In some embodiments, a sweetener composition can comprise a carrier compound and one or more sweetener carbohydrates and/or sweetener polyols in an amount (weight/weight) of between about 6-9% carrier compound (wt/wt). In some embodiments, a sweetener composition can comprise a carrier compound and one or more sweetener carbohydrates and/or sweetener polyols in an amount (weight/weight) of between about 6-12% carrier compound (wt/wt) relative to total sweetener. In some embodiments, a sweetener composition can comprise a carrier compound and a one or more sweetener carbohydrates and/or sweetener polyols in an amount (weight/weight) of between about 8-10% carrier compound (wt/wt) relative to total sweetener. In some embodiments, a sweetener composition can comprise a carrier compound and one or more sweetener carbohydrates and/or sweetener polyols wherein the sweetener composition comprises up to 10 wt % carrier compound relative to the total weight of the composition. In some embodiments, a sweetener composition can comprise a carrier compound and one or more sweetener carbohydrates and/or sweetener polyols wherein the sweetener composition comprises 8 wt % carrier compound.

In some cases when the carrier compound is silica, the sweetness of a sweetener composition can have a ratio of silica to sweetener carbohydrate and/or sweetener polyol that gives a maximum sweetness. Increasing the amount of silica relative to sweetener carbohydrate and/or sweetener polyol beyond the maximum point can decrease the sweetness of the composition. In some cases, wherein the amount of silica is higher than the maximum sweetness amount, a grainy, sandy, or chalky characteristic can enter the taste profile. In some cases, when the amount of silica is less than the maximum sweetness amount, the composition does not fully benefit from the sweetness enhancement effect of the silica. In some cases, the maximum sweetness amount is between about 6-12% carrier compound (wt/wt relative to the sweetener carbohydrate and/or sweetener polyol). In some cases, the maximum sweetness amount is between about 8-10% carrier compound (wt/wt relative to the sweetener carbohydrate and/or sweetener polyol). In some cases, the maximum sweetness amount is about 8% carrier compound (wt/wt relative to the sweetener carbohydrate and/or sweetener polyol).

Additives and Formulations

The sweetener compositions disclosed herein can comprise additional food additives. In some embodiments, the sweetener compositions disclosed herein comprise up to 0.001, 0.01, 0.1, 0.5, 1, 1.5, 2, 2.5, 3, 4, 5, 6, 7, 8, 9, 10, 20, 30, 40, 50, 60, 70, 80, or 90 wt % food additives. In some embodiments, the sweetener compositions disclosed herein comprise at least 0.001, 0.01, 0.1, 0.5, 1, 1.5, 2, 2.5, 3, 4, 5, 6, 7, 8, 9, 10, 20, 30, 40, 50, 60, 70, 80, or 90 wt % food additives. Food additives can be materials safe to digest. Food additives can add volume and/or mass to a composition. Some non-limiting examples of a food additive include food coloring, natural flavoring, artificial flavoring, batch marker, food stabilizer, food acid, filler, anticaking agent, antioxidant, bulking agent, color retention agent, emulsifier, humectant, thickener, pharmaceutical excipient, solid diluent, sweetener, artificial sweetener, natural sugar substitute, and preservative, for example. Some non-limiting examples of food additives are silica, silicon dioxide, cellulose, microcrystalline cellulose, powdered cellulose, starch, modified food starch, amylum, calcium carbonate, maltodextrin, hemicellulose, cyclodextrins, hydroxyalkyl cyclodextrins, inulin, pectin, chitin, chitosan, carrageenans, agar, natural gums (e.g., gum arabic, gellan gum, guar gum, locust bean gum, and xanthan gum), and magnesium stearate. A food additive differs from a carrier compound, as food additives are not coated with the sweetener carbohydrate and/or sweetener polyol. A food additive differs from a sweetener carbohydrate or sweetener polyol, as food additives do not coat the carrier compound. In some cases, a compound can function as one or more of a carrier compound, a food additive, and a sweetener carbohydrate or sweetener polyol, wherein the carrier compound is coated with the sweetener carbohydrate and/or sweetener polyol. In some embodiments, a food additive is a combination of more than one distinct food additives.

The sweetener compositions disclosed herein can further comprise an artificial sweetener, a natural sugar substitute, or a combination thereof. In some embodiments, the sweetener compositions disclosed herein comprise up to 0.001, 0.01, 0.1, 0.5, 1, 1.5, 2, 2.5, 3, 4, 5, 6, 7, 8, 9, or 10 wt % artificial sweetener, a natural sugar substitute, or a combination thereof. In some cases, the artificial sweetener is selected from the group consisting of: acesulfame potassium, advantame, alitame, aspartame, sodium cyclamate, dulcin, glucin, neohesperidin dihydrochalcone, neotame, P-4000, saccharin, aspartame-acesulfame salt, and sucralose. In some cases, the natural sugar substitute is selected from the group consisting of: brazzein, curculin, glycyrrhizin, glycerol, inulin, mogroside, mabinlin, malto-oligosaccharide, mannitol, miraculin, monatin, monellin, osladin, pentadin, stevia (including partly stevia components), tagatose, and thaumatin.

Summary of Compositions

In some cases, a sweetener composition comprises: at least one sweetener carbohydrate such as glucose, sucrose, maltose, lactose, high fructose corn syrup, or high maltose corn syrup; and/or at least one sweetener polyol such as xylitol, maltitol, erythritol, sorbitol, threitol, arabitol, hydrogenated starch hydrolysates (HSH), isomalt, lactitol, mannitol, galactitol (dulcitol); and 6-12% carrier compound wt/wt relative to a sum of total sweetener (sweetener carbohydrates and sweetener polyols). In some cases, the composition is 8-10% carrier compound or about 8% carrier compound wt/wt relative to a sum of total sweetener. In some cases, the carrier compound is chitosan or silica such as Perkasil® (W. R. Grace & Co).

The compositions described herein can be purified sweetener compositions which are substantially homogenous. In some cases, the compositions are solid, isolated sweetener compositions consisting essentially of one or more sweetener carbohydrates and/or sweetener polyols and a carrier compound. The compositions can be powders with small particle sizes. The particle sizes of the compositions described herein can be measured. For example, the particles can be measured by DLS (dynamic light scattering). The distribution of particle sizes can be measured by size fractionation of particles using sieves with openings of different sizes. In some cases, the distribution of particle sizes in the composition can be used to characterize the composition and/or its physical properties. For example, the perceived sweetness of sweetener composition described herein may be correlated to the distribution of particle sizes. In some cases, at least 10, 20, 30, 40, 50, 60, 70, 80, or 90 percent of the particles of the compositions described herein are between about 25 microns and about 200 microns in diameter. In some cases, at least 10, 20, 30, 40, 50, 60, 70, 80, or 90 percent of the particles of the compositions described herein are less than or equal to 74 microns in diameter. In some cases, at least 10, 20, 30, 40, 50, 60, 70, 80, or 90 percent of the particles of the compositions described herein are at least 25 microns in diameter. In some cases, at least 10, 20, 30, 40, 50, 60, 70, 80, or 90 percent of the particles of the compositions described herein are between about 25 microns and about 74 microns in diameter.

The compositions described herein can have enhanced sweetness. In some cases, the sweetener composition has enhanced sweetness compared to a control composition; wherein the control composition consists of the same contents by identity and quantity of the sweetener composition but without the carrier compound.

Applications of Sweetener Compositions

In some embodiments, a composition provided herein is used as a sweetener for a food or a consumable product. In some embodiments, a food or a consumable product comprises a composition provided herein, wherein the food or the consumable product is confectionary, chocolate, baked goods, condiments, sauces, dressings, tooth paste, chewing gum, pharmaceutical syrups, or dairy products. In some embodiments, the food or consumable product contains up to 0.1, 0.5, 1.0, 1.1, 1.2, 1.3, 1.4, 1.5, 1.6, 1.7, 1.8, 1.9, or 2.0% silica wt/wt.

In some embodiments, a food or a consumable product with enhanced sweetness, lower caloric value, or both enhanced sweetness and lower caloric value is obtained by substituting one or more sweetener carbohydrates and/or sweetener polyols for a composition comprising the one or more sweetener carbohydrates and/or sweetener polyols and a carrier compound. In some embodiments, a method of producing a food or a consumable product with enhanced sweetness, lower caloric value, or both enhanced sweetness and lower caloric value comprises substituting one or more sweetener carbohydrates and/or sweetener polyols in the food or the consumable product for a composition comprising a comparable amount of the one or more sweetener carbohydrates and/or sweetener polyols and a carrier compound.

Enhanced sweetness can refer to a composition that produces a stronger or higher sense of sweetness to a human. Compositions with enhanced sweetness taste sweeter than the composition to which they are compared. In some embodiments, a smaller amount (by weight or by volume) of a composition with enhanced sweetness will produce the same sense of sweetness as a larger amount (by weight or by volume) of the composition that lacks enhanced sweetness. In some embodiments, enhanced sweetness is measured by a taste test. In some embodiments, sweetness is measured by a blind taste test. In some embodiments, a composition with enhanced sweetness will produce a higher perceived sweetness and a lower caloric content than a comparable amount (by weight or by volume) of a composition that lacks enhanced sweetness.

The sweetener composition provided herein can have a quantified enhanced sweetness. For example, the sweetener composition provided herein can have the sweetness enhanced by at least 5, 10, 20, 30, 40, 50, 60, 70, 80, 90 or 100% relative to a control. For example, the sweetness can be enhanced by 10-80%, 20-70%, or 40-60%. One non-limiting example of a taste test method to measure enhanced sweetness is to taste a set amount of a control composition, and then taste varying amounts of the sweetener composition to be tested to find the amount of sweetener that corresponds to the sweetness of the control composition. The enhanced sweetness can be calculated by the following formula: [amount of control sweetener−amount of sweetener required for equal sweetness]/[amount of control sweetener]. For example, varying amounts of a sweetener composition described herein (e.g. 5, 4, 3, 2 and 1 mg of a composition comprising 92% sucrose and 8% Perkasil) are tasted to find an equal sweetness to a control composition (e.g. 5 mg sucrose). The test shows that 3 mg of the composition gives an equal sweetness to 5 mg of sucrose control. In this case, the enhanced sweetness is (5−3)/5=40%.

The compositions described herein can function as bitterness reducers and, in some instances, as bitterness masking agents. For example, adding a composition described herein to a food or a consumable product can reduce or mask a bitter taste. In some cases, a composition described herein can be added to a bitter food or consumable product to increase the sweetness of the food or consumable product and decrease the bitterness. In some cases, a sweetener composition as described herein can reduce the bitterness of a medicine or pharmaceutical. For example, a method of reducing bitterness in a medicine or pharmaceutical can comprise adding a composition described herein to the medicine or pharmaceutical. Reducing the bitterness of a medicine can have the beneficial effect of increasing patient compliance and increased desire to take a medicine, particularly with pediatric patients.

In some cases, a composition described herein can be added to a food or consumable product to produce at least one of the characteristics selected from the group consisting of increased sweetness, increased creamy aftertaste, decreased bitter aftertaste, decreased mouth drying aftereffect, decreased metallic aftertaste, decreased liquorice aftertaste, or reduced caloric value of the food or consumable product. In some cases, a composition described herein can be added to a food or consumable product to produce at least two of the characteristics selected from the group consisting of increased sweetness, increased creamy aftertaste, decreased bitter aftertaste, decreased mouth drying aftereffect, decreased metallic aftertaste, decreased liquorice aftertaste, or reduced caloric value of the food or consumable product. In some cases, a composition described herein can be added to a food or consumable product to produce at least three of the characteristics selected from the group consisting of increased sweetness, increased creamy aftertaste, decreased bitter aftertaste, decreased mouth drying aftereffect, decreased metallic aftertaste, decreased liquorice aftertaste, or reduced caloric value of the food or consumable product.

Sensory Testing

The sweetener composition described herein produces a higher perceived sweetness than a comparable amount (by weight) of the one or more sweetener carbohydrates and/or sweetener polyols in free, unassociated form. In some embodiments, a composition comprising a carrier compound and one or more sweetener carbohydrates and/or sweetener polyols produces a higher perceived sweetness than a control composition; wherein the control composition does not comprise the carrier compound, and the control composition comprises a comparable amount (by weight) of the one or more sweetener carbohydrates and/or sweetener polyols in free, unassociated form. For example, 1.0 grams of a composition comprising about 0.08 grams of a carrier coated with about 0.92 grams of one or more sweetener carbohydrates and/or sweetener polyols produces a higher perceived sweetness than a control composition that does not comprise the carrier compound and the control composition comprises about 0.92 grams of the one or more sweetener carbohydrates and/or sweetener polyols.

Enhanced sweetness can be determined by a sensory test. Equivalent sweetness with a lower caloric value can be determined by a sensory test. In some cases, the sensory test is a taste test. In some cases, the taste test is a screening test, a professional taste test, or a market research test. In some cases, a screening test is performed by at least 1, 2, 3, 4, 5, 6, 7, 8, or 9 taste testers. In some cases, a professional taste test is performed by at least 10, 15, 20, 25, or 30 taste testers. In some cases, a market research test is performed by at least 31, 40, 50, 60, 70, 80, 90, 100, 150, 200, 300, 400, or 500 taste testers.

A sensory test can use one or more various protocols. For example, in some cases, a sensory test can be the "triangle method", follow ISO requirements, or a combination thereof. In some cases, the taste test can be the average of multiple trials. For example, each taste tester can consume multiple sweetener compositions or food products comprising a sweetener composition and attempt to sequence them by relative sweetness. Alternatively or in combination, a taste test can comprise tasting a standard, and determining whether a tested composition is more or less sweet than the standard.

A taste tester can be a person with average taste perception. In some cases, a taste tester can be a professional taste tester. In some cases, a taste tester can be a person who has passed a tasting exam by correctly identifying foods or food components. Alternatively or in combination, a taste tester can be a person who can identify the relative amounts of a taste or flavor. For example, a taste tester can be a person who can correctly sequence varying amounts of sugar in water.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1: Formation of a Sweetener Composition

Sucrose (80 g., pure, food-grade) and silica (6.4 g., Perkasil® SM 660, pure, food-grade, produced by W. R.

Grace & Co) are combined in a Moulinex® coffee grinding machine. The solids are ground together for 20 sec to form a powder (8% silica wt/wt in sucrose). The solids are transferred to an electric mortar and pestle. The upper pestle pressure is set at a scale reading of 6.5. The scraper is adjusted as closed 6.5 rounds from minimal contact with the mortar side. The contact of the pestle with the mortar side is adjusted as closed 11.5 rounds from minimal contact. The mixture is ground for 5 minutes using the mortar and pestle. The combined powdered mixture is optionally sonicated for 30 min at 40° C. at 40 KHz. The mixture is then passed through a sieve (70 mesh) to remove larger particles. The powder that passes through the sieve is labeled as composition S1.

Example 2: Size Fractionation of Sweetener Compositions

Size fractionation is performed on the composition S1 of Example 1 by passing the composition through sieves with successively smaller openings to determine the particle size distribution of the composition as shown in Table 2.

TABLE 2

| Size Range (micron) | % Weight |
|---|---|
| 74-200 | 23 |
| 53-74 | 8 |
| 37-53 | 12 |
| 25-37 | 39 |
| <25 | 18 |

Example 3: Formation of Sweetener Compositions

A) 8% Silica in Sucrose—Powder Preparation:

Silica (4.0 g., Perkasil® SM 660, pure, food-grade) is transferred into a mechanical grinder and ground for 20 sec. The silica is then transferred into a mortar and pestle for further grinding for 10 min. Sucrose (50 g., pure, food-grade) is ground in a mechanical grinder (Moulinex® grinder) for 20 sec. The sucrose is added in portions to the mortar and pestle for further grinding with the silica for 10 min. Once all the sucrose is added, the mixture is ground for 5 more minutes using the mortar and pestle. The combined powdered mixture is sonicated for 30 min at 40° C. then put through a sieve (70 mesh) to remove larger pieces. The powder that passed through the sieve is labeled as composition 3A.

B) 8% Silica in Sucrose Syrup:

Sucrose (70 g, pure, food-grade) is transferred into a mechanical grinder and ground for 20 sec. The ground sugar is transferred into a mortar and pestle for another 10 min of grinding. The ground sample is transferred in portions into 37.7 gr deionized water previously heated to 70° C. (while stirring) until a clear yellowish solution is achieved (yielding a solution of 65:35 ratio between sucrose and water). Silica (5.6 g, Perkasil® SM 660, pure, food-grade, 8% relative to sucrose) is added to the sucrose syrup in portions (while stirring). The resulting solution is stirred vigorously for 10 more minutes. The dispersion is sonicated at 40° C. for 30 min and labeled as composition 3B.

C) Sucrose Syrup:

70 gr of sucrose ground mechanically and physically, are transferred in portions to 37.7 gr deionized water previously heated to 70° C. A clear yellowish solution is achieved (65:35 ratio between sucrose and water). The clear solution is stirred vigorously for 10 more minutes. The dispersion is sonicated at 40° C. for 30 min and labeled as composition 3C.

Example 4: Tasting Sweetener Compositions of Example 3

Three testers are each given two sets of triangle tests to taste the sweetener compositions. The results are displayed in the tables herein. The "+" is the label for the sample with the highest perceived sweetness.

Test 4A (Powders):

Each tester is given 4 mg of the following powdered samples: Pure sucrose and 3A.

TABLE 4A

| | Test 1 | | Test 2 | | |
|---|---|---|---|---|---|
| Sample: | sucrose | 3A | sucrose | 3A | 3A |
| Taster 1 | + | | | | + |
| Taster 2 | + | | | | + |
| Taster 3 | | + | | + | + |

Test 4B (Syrups):

Each tester is given 4 mg of the following syrup samples: 3B and 3C.

TABLE 4B

| | Test 1 | | | Test 2 | | |
|---|---|---|---|---|---|---|
| | 3B | 3C | 3C | 3C | 3B | 3B |
| Taster 1 | + | | | | | + |
| Taster 2 | + | | + | + | | + |
| Taster 3 | + | | | | + | + |

Test 4C (Solutions):

Each tester is given about 5 ml taken from two stock samples: i) 10 g of sucrose in 500 mL deionized water and ii) 10 g of 3A in 500 mL deionized water.

TABLE 4C

| | Test 1 | | | Test 2 | | |
|---|---|---|---|---|---|---|
| | sucrose | sucrose | 3A | sucrose | 3A | 3A |
| Taster 1 | | + | + | | + | + |
| Taster 2 | | + | + | + | | + |
| Taster 3 | | | + | | + | + |

Example 5: Formation of Chocolate Comprising Enhanced Sweetener Compositions

The sample chosen as the enhanced sucrose added in all cream preparation is composition 3A (described in example 3-8% Perkasil® in sucrose, dry preparation). Dark chocolate with no added sugar by "Galler chocolatier" (25 g) is slowly melted in a hot water bath. As the chocolate melted, about 7 gr of milk is added in portions until a creamy soft texture is reached. The sweetener or sugar is added to the melted chocolate and stirring continued. The mixture is cooled to room temperature. The compositions of Chocolate 5A-5D are made of ingredients as depicted in the following table:

| Ingredients | Chocolate 5A | Chocolate 5B | Chocolate 5C | Chocolate 5D |
|---|---|---|---|---|
| Chocolate | 25 | 25 | 25.258 | 25.267 |
| Milk | 7 | 7 | 7.022 | 7.023 |
| sweetener | None | Sucrose - 25 mg | 3A - 20 mg | 3A - 25 mg |

Example 6: Taste Test of Chocolate Compositions of Example 5

Three taste testers are given a small sample from 4 types of chocolate. The details of the chocolate preparation are described in Example 5. The results of the taste test are described in Table 6.

TABLE 6

| | Chocolate 5A | Chocolate 5B | Chocolate 5C | Chocolate 5D |
|---|---|---|---|---|
| Tester 1 | Bitter and slightly sweet | Sweeter slightly less bitter | Not as bitter and sweeter | The sweetest sample Weak bitterness |
| Tester 2 | Bitter and slightly sweet | Sweeter slightly less bitter | Not as bitter and sweeter Has a bit of an unpleasant lingering | Same as previous, less of the lingering sensation Very similar to the previous sample |
| Tester 3 | Bitter and slightly sweet | Sweeter slightly less bitter | Not as bitter and sweeter | The sweetest sample Weak bitterness |

Example 7: Formation and Tasting of Bitterness Reduced Paracetamol

A tablet of a known bitter medicine, paracetamol ("Acamol™" by Teva, also known as acetaminophen) is crushed. Several 3 mg portions of the crushed medicine are weighed in separate dishes. A drop of about 10 mg sweetener is added to each portion. This is repeated both with two sweetener syrups: i) sucrose syrup (65 g sucrose in 35 g water) and ii) enhanced syrup (7 g Perkasil® added to a syrup of 65 g sucrose in 35 g water at 75° C.). The results are disclosed in Table 7.

TABLE 7

| Taster | Paracetamol + sucrose syrup | Paracetamol + enhanced sucrose syrup |
|---|---|---|
| Tester 1 | Very bitter No sweetness | Less bitter, sweeter, A huge difference |
| Tester 2 | Extremely bitter | The sample is still bitter but significantly less and sweeter |
| Tester 3 | Extremely bitter | The sample is still bitter but significantly less and sweeter |

Example 8: Formation of Sweetener Compositions Comprising Chitosan Carrier Compound Chitosan (Kiofine® B, 50μ particle size) is used in the preparation of the following samples:
A) 8% Chitosan in sucrose dry sample: 15 gr of sucrose are transferred into a mechanical grinder, 1.2 gr (8%) of chitosan is added, the mixture is ground for 20 sec. After a sample is taken, the mixture is transferred into a mortar and pestle for another 10 min of grinding. A sample is taken from the ground mixture. The remaining ground mixture is sonicated for 30 min at 40° C. The sample is passed through a sieved and labeled 8A.
B) 8% Chitosan in sucrose syrup where the dry mixed powder is added to water at 70° C. 6 g of the sieved and ground mixture of chitosan in sucrose (from compound 8A) is transferred in portions to 3 gr of deionized water at 70° C. The dispersion is stirred vigorously for about 10 min. The dispersion is sonicated at 40° C. for 30 min. The resulting chitosan syrup is opaque and with a dark orange color. The resulting starch syrup is opaque and white. A sample of the starch syrup is dried in an oven at 90° C. for 72 hours and labeled 8B.
C) 8% Chitosan in sucrose syrup where the Chitosan is added to the sucrose syrup. 10 g of sucrose (ground mechanically and manually) is transferred in portions into 5.4 g deionized water previously heated to 70° C. (while stirring) until a clear yellowish solution is achieved (yielding a solution of 65:35 ratio between sucrose and water). 0.8 gr (8%) of chitosan is added to the sucrose syrup in portions (while stirring). The resulting dispersion is stirred vigorously for 20 more minutes. Following stirring, the solution is sonicated at 40° C. for 30 min. The resulting syrup is opaque and with a dark orange color. The resulting starch syrup is opaque and white. A sample of the chitosan syrup is dried in an oven at 90° C. for 72 hours and labeled 8C.

Example 9: Tasting of Sweetener Compositions Comprising Chitosan

Each tester is given 4 mg of sucrose and 8A solid and 6 mg from each syrups 8B and 8C. The results are shown in Table 9.

TABLE 9

| Taster | Sucrose | 8A | 8B | 8C |
|---|---|---|---|---|
| Taster 1 | X | X+ After taste | X+ Slightly sweeter | X+ Barely, not as impressive as the powder samples |
| Taster 2 | X | More than X+ | X+ | X+ |
| Taster 3 | X | X+ After taste | X+ Residual | X |
| Taster 4 | X | X After taste | X | X+ more than previous |
| Taster 5 | X | X+ After taste | X+ Very slightly, after taste | X+ |

Key:
X represents a level of sweetness,
X+ represents a taste that is more sweet than X Example 10: Sweetener Compositions Comprising Glucose Monohydrate The following general procedure is used to make each composition 10A-10F: Glucose monohydrate (15 g, pure, food-grade) is transferred into a mechanical grinder, 1.10 gr (8%) of carrier compound is added, and the mixture is ground for 20 sec. After a sample is taken, the mixture is transferred into a mortar and pestle for another 10 min of grinding. A sample is taken from the ground mixture. The remaining ground mixture is sonicated for 30 min at 40° C. and then passed through a sieve (70 mesh).

This experiment is repeated for each sample 10A-10E, selecting the carrier compound to produce compositions as follows:

10A—Glucose monohydrate (no carrier compounds used)—ground and sieved

10B—8% Perkasil® in glucose monohydrate

10C—8% CN001 (chitosan 200 nm particle size) in glucose monohydrate

10D—8% SCP-1 (chitosan 200 mesh particle size) in glucose monohydrate

Example 11: Taste Test of Sweetener Compositions Comprising Glucose Monohydrate Each taster is given 4 mg of each of the solid sweetener compositions. The results are described in Table 11 (with a repetition of 10C and 10D.).

TABLE 11

| Taster | Glucose monohydrate 10A | 10B | 10C | 10C | 10D | 10D |
|---|---|---|---|---|---|---|
| Taster 1 | X Barely any sweetness | X++ | X+ | X+ | X+ Very weak | X Weak |
| Taster 2 | X Barely any sweetness | X++ | X+ | X+ | X+ | X Weak |
| Taster 3 | X Barely any sweetness | X++ | X+ Slightly, spread | X+ Very slightly sweeter | X+ Very weak | X Weak |

Key:
X represents a level of sweetness,
X+ represents a taste that is more sweet than X,
X++ represents a taste that is more sweet than X+

Example 12: Formation of Sweetener Compositions with Other Carrier Compounds 15 gr of sucrose are transferred into a mechanical grinder, 1.2 gr (8%) of carrier are added, and the mixture is ground for 20 sec. After a sample is taken, the mixture is transferred into a mortar and pestle for another 10 min of grinding. A sample is taken from the ground mixture. The remaining ground mixture is sonicated for 30 min at 40° C. Samples are sieved (70 mesh). Each taster is given 4 mg of the following samples and the results are shown in Table 12:

12A—Sucrose

12B—8% CN001 (Chitosan, particle size—200 nm) in sucrose

12C—8% FGC-2 (Chitosan, particle size—80 mesh) in sucrose

12D—8% Avicel® LM 310 (Maltodextrin) in sucrose

12E—8% Avicel® GP 1030 (Maltodextrin) in sucrose

TABLE 12

| Taster | Sucrose 12A | 12B (Chitosan 200 nm) | 12C (Chitosan, 80 mesh) | 12D (Maltodextrin-Avicel® LM 310) | 12E (Maltodextrin-Avicel® GP 1030) |
|---|---|---|---|---|---|
| Taster 1 | X | X++ | X+ | X+ A bit less than 143 | X+ A bit less than previous |
| Taster 2 | X | X++ | X+ | X+ A bit less than 143 | X+ Better texture |

Key:
X represents a level of sweetness,
X+ represents a taste that is more sweet than X,
X++ represents a taste that is more sweet than X+

Example 13: Formation of Sweetener Compositions with Other Carrier Compounds 15 gr of sucrose are transferred into a mechanical grinder, 1.2 gr (8%) of carrier compound is added, and the mixture is ground for 20 sec. After a sample is taken, the mixture is transferred into a mortar and pestle for another 10 min of grinding. A sample is taken from the ground mixture. The remaining ground mixture is sonicated for 30 min at 40° C.

13A—Sucrose

13B—8% CN001 (Chitosan, particle size—200 nm) in sucrose

13C—8% CN002 (Chitosan, particle size—200 nm) in sucrose

13D—8% SCP-1 (Chitosan, particle size—200 mesh) in sucrose

13E—8% SCP-2 (Chitosan, particle size—200 mesh) in sucrose

13F—8% FGC-2 (Chitosan, particle size—80 mesh) in sucrose

13G—8% Avicel® LM 310 (Maltodextrin) in sucrose

13H—8% Avicel® GP 1030 (Maltodextrin) in sucrose

Samples are sieved. Each taster is given 4 mg of the following samples and the results are shown in

TABLE 13

| Taster | Sucrose 13A | 13B | 13C | 13D | 13E | 13F | 13G | 13H |
|---|---|---|---|---|---|---|---|---|
| Taster 1 | X | X++ | X++ | X++ | X+ | X+ | X+ | X+ small |
| Taster 2 | X | X+ | X++ | X++ | X+ | X++ | X+ | X+ small |
| Taster 3 | X | X++ | X++ | X++ | X+ | X++ Maybe more | X+ | X+ small |

Key:
X represents a level of sweetness,
X+ represents a taste that is more sweet than X,
X++ represents a taste that is more sweet than X+

Example 14: Sensory Test Procedure

The tests are participated by a panel of 8 tasting experts who have been sensory tested in the past. All participants have been trained. The tests are divided into the following 4 segments:

a) Testing the tasters sensory threshold b) Calibration c) Sucrose versus S1 composition tastings—in powder and syrup form d) Sucrose versus S1 composition tastings—powders mixed in a separate medium Tasting process: All tasting stages excluding calibration, are conducted in the form of a "triangle test": each participant is given three samples marked with random numbers that include two identical samples and one dissimilar sample. Participants are instructed to name the different sample in each set and explain the difference in their opinion.

Participants are given two sets of tests in each tasting, where one test included a single reference sample and the other contained two.

Sensory threshold: Panel participants are given seven triangle tests that included various concentrations of sucrose dissolved in water.

Calibration step: This step is added to the tasting process as another form of tasting the panel's sensory threshold for sweetness. All panel members are given two samples of sucrose marked "A" and "B" the samples were of 4 mg and 5 mg respectively in the purpose of testing the panel's ability to recognize such delicate variations.

The rest of the tests were conducted similarly—each sample is tested with sucrose as reference in two sets of triangle tests.

Example 15: Amount of Perkasil® in Sweetener Compositions

Several compositions are prepared as described herein (Example 3) but the amount of Perkasil® is varied among samples and taste testers consume 4 mg of each sample to judge the taste and sweetness with respect to amount of Perkasil®. The results are displayed in Table 15 (each "+" indicates more sweetness).

TABLE 15

| | Sucrose syrup | 6% Perkasil® - mixed powders to sucrose syrup | 6% Perkasil® - Perkasil added to sucrose syrup | 10% Perkasil® - mixed powders to sucrose syrup | 10% Perkasil® - Perkasil added to sucrose syrup |
|---|---|---|---|---|---|
| Tester 1 | X | X+ Small variation | X+ Small variation | X++ 1.5 times sweeter than sucrose Residual taste | X+ |
| Tester 2 | X | X+ Small variation | X+ | X+ | X |
| Tester 3 | X | X+ Small variation, Different texture | X+ Different texture | X++ 1.5 times sweeter than sucrose Residual taste | X+ |
| Tester 4 | X | X+ Small variation | X+ Small variation | X+ Small variation | X+ |

Key:
X represents a level of sweetness,
X+ represents a taste that is more sweet than X,
X++ represents a taste that is more sweet than X+

It is noted that the 6% and 10% Perkasil® compounds are sweeter than the sucrose syrup composition that lacks Perkasil®. Additionally, the compositions with 6% and 10% Perkasil are less sweet than the corresponding 8% Perkasil® composition.

Example 16: Formation of Sweetener Compositions Comprising Sweetener Polyol

A) 1.0 gram of Maltitol and 0.08 gram Perkasil® are ground together as solids manually using a mortar and pestle for 10 min to form an maltitol sweetener composition with 8% silica wt/wt. The resulting powdered mixture is sonicated at 40° C. for 30 min, then sieved (70 mesh). The resulting sweetener composition, 16A, is stored in a refrigerator until tested.

B) Sorbitol (5.0 gram) and Perkasil® (0.4 gram) are ground together for 20 sec in a mechanical Moulinex grinder. The resulting mixture is transferred to a mortar and pestle and ground manually for 10 min. The resulting powdered mixture is sonicated at 40° C. for 30 min and then sieved to produce the final sweetener composition comprising sorbitol and Perkasil® (8% wt/wt), 16B.

C) Xylitol (5.0 gram) and Perkasil® (0.4 gram) are ground together for 20 sec in a mechanical Moulinex grinder. The resulting mixture is transferred to a mortar and pestle and ground manually for 10 min. The resulting powdered mixture is sonicated at 40° C. for 30 min and then sieved to produce the final sweetener composition comprising xylitol and Perkasil® (8% wt/wt), 16C.

Example 17: Taste Test of Sweetener Compositions Comprising Sweetener Polyols Tasters each consume a sample of 5 mg of each of the following 6 sweetener compositions: maltitol, 16A, sorbitol, 16B, xylitol, and 16C, and record their observations after each test. The observations are recorded in the following table:

| | Maltitol | 16A | Sorbitol | 16B | Xylitol | 16C |
|---|---|---|---|---|---|---|
| Tester 1 | After taste, barely sweet X | X+ | Sweeter than Maltitol Y | Y | Sweetest polyol so far Z | Z++ |
| Tester 2 | Some sweetness X | X+ | Much sweeter than Maltitol Y | Y+ | Very sweet Zn | Z+ |
| Tester 3 | Some sweetness X | X++ | Less sweet than Maltitol Y | Y + 0.5 | Sweeter than sucrose Z | Z + 1.5 |

-continued

| | Maltitol | 16A | Sorbitol | 16B | Xylitol | 16C |
|---|---|---|---|---|---|---|
| Tester 4 | Less than sucrose X | X + 0.5 | Similar to Glucose Y | Y + fades | As sweet as Sorbitol, fades Z | Z+ |
| Tester 5 | Less than sucrose X | X + 0.5 | Fades Y | Y + 0.5 | Very sweet fades quickly Z | Z + 0.5 Sample Spread |

Key:
X represents a level of sweetness,
X+ represents a taste that is more sweet than X,
X++ represents a taste that is more sweet than X+.
Y represents a level of sweetness,
Y+ represents a taste that is more sweet than Y,
Y++ represents a taste that is more sweet than Y+.
Z represents a level of sweetness,
Z+ represents a taste that is more sweet than Z,
Z++ represents a taste that is more sweet than Z+.

Example 18: Formation of Sweetener Compositions Comprising High Intensity Sweeteners and Sucrose A) Aspartame (5 mg) and sucrose (1.0 gram) are ground together manually with a mortar and pestle for 10 min. The resulting mixture is sonicated at 40° C. for 30 min, and the powdered mixture is sieved to produce the product sweetener composition 18A.

B) Acesulfame potassium (Acesulfame K) (10 mg) and sucrose (2.0 gram) are ground together manually with a mortar and pestle for 10 min. The resulting mixture is sonicated at 40° C. for 30 min, and the powdered mixture is sieved to produce the product sweetener composition 18B.

C) A gram scale portion (e.g. about 1.0 gram) of saccharin is ground in a Moulinex mechanical grinder for to reduce the particle size. A small portion of the ground saccharin (10 mg) is combined with sucrose (2.0 gram), and the solids are ground together manually with a mortar and pestle for 10 min. The resulting mixture is sonicated at 40° C. for 30 min, and the powdered mixture is sieved to produce the product sweetener composition 18C.

D) Sodium cyclamate (10 mg) and sucrose (2.0 gram) are ground together manually with a mortar and pestle for 10 min. The resulting mixture is sonicated at 40° C. for 30 min, and the powdered mixture is sieved to produce the product sweetener composition 18D.

Example 19: Formation of Sweetener Compositions Comprising High Intensity Sweeteners, Sucrose, and Silica A) Aspartame (10 mg), sucrose (2.0 gram), and Perkasil® SM 660 (0.16 gr) are ground together manually with a mortar and pestle for 10 min. The resulting mixture is sonicated at 40° C. for 30 min, and the powdered mixture is sieved to produce the product sweetener composition 19A.

B) Acesulfame K (10 mg), sucrose (2.0 gram), and Perkasil® SM 660 (0.16 gr) are ground together manually with a mortar and pestle for 10 min. The resulting mixture is sonicated at 40° C. for 30 min, and the powdered mixture is sieved to produce the product sweetener composition 19B.

C) A gram scale portion of saccharin is ground in a Moulinex mechanical grinder to reduce the particle size. A small portion of the ground saccharin (10 mg) is combined with Perkasil® SM 660 (0.16 gr), and sucrose (2.0 gram), and the solids are ground together manually with a mortar and pestle for 10 min. The resulting mixture is sonicated at 40° C. for 30 min, and the powdered mixture is sieved to produce the product sweetener composition 19C.

D) Sodium cyclamate (10 mg), sucrose (2.0 gram), and Perkasil® SM 660 (0.16 gr) are ground together manually with a mortar and pestle for 10 min. The resulting mixture is sonicated at 40° C. for 30 min, and the powdered mixture is sieved to produce the product sweetener composition 19D.

Example 20: Taste Test of Sweetener Compositions Comprising High Intensity Sweeteners, Sucrose and Optionally Silica Each taster consumes a sample of each of the following 8 samples: 18A, 18B, 18C, 18D, 19A, 19B, 19C and 19D, and records their observations after each test. The amount of each sample given to each tester is normalized by the sweetness factor of the High Intensity Sweetener included according to the following table:

| Sweetener | RS (of pure sweetener) | Sweetness intensity (of sample) | Tasting sample weight [mg] |
|---|---|---|---|
| Aspartame | 200 | 2 | 2.5 |
| Acesulfame K | 200 | 2 | 2.5 |
| Saccharin | 300 | 2.5 | 2 |
| Sodium cyclamate | 40 | 1.2 | 4.2 |

Thus, each tester consumes 2.5 mg of samples comprising Aspartame (18A and 19A), 2.5 mg of samples comprising Acesulfame K (18B and 19B), 2.0 mg of samples comprising Saccharin (18C and 19C), and 4.2 mg of samples comprising Sodium cyclamate (18D and 19D).

The observations made by each tester are recorded in the following table:

| | Aspartame | | Acesulfame K | | Saccharin | | Sodium cyclamate | |
|---|---|---|---|---|---|---|---|---|
| | 18A | 19A | 18B | 19B | 18C | 19C | 18D | 19D |
| Taster 1 | Sweet, less than sucrose, no bitterness X | X++ | Sweet with a metallic after taste Y | Y+ Less after taste | Sweet with a metallic after taste, leaves a sense of dryness Z | Increased after taste | Sweet with a cardboard after taste A | A+ Sweeter with enhanced after taste |
| Taster 2 | Sweeter than | X | Sweet (less | Y+ No after | Very sweet Z | Z++ | Sweet A | A+ |

-continued

| | Aspartame | | Acesulfame K | | Saccharin | | Sodium cyclamate | |
|---|---|---|---|---|---|---|---|---|
| | 18A | 19A | 18B | 19B | 18C | 19C | 18D | 19D |
| | sucrose, different sweetness X | | than X) no after taste Y | taste | | | | |
| Taster 3 | Sweeter than sucrose, lingers X | X The same | After taste Y | Y+ After taste | Very sweet, a sense of dryness Z | Z Same as NG363 | Sweetest HIS so far No after taste A | Cardboard after taste |
| Taster 4 | Less than sucrose X | X After taste | Weak sweetness, after taste Y | Y+ Slightly less after taste | Very sweet, a sense of dryness Z | Z++ Very sweet, increased after taste | Very sweet (slightly more than NG363) A | A+ Sweet with a cardboard after taste |

Key:
X represents a level of sweetness,
X+ represents a taste that is more sweet than X,
X++ represents a taste that is more sweet than X+.
Y represents a level of sweetness,
Y+ represents a taste that is more sweet than Y,
Y++ represents a taste that is more sweet than Y+.
Z represents a level of sweetness,
Z+ represents a taste that is more sweet than Z,
Z++ represents a taste that is more sweet than Z+.
A represents a level of sweetness,
A+ represents a taste that is more sweet than A.

Example 21: Formation of Sweetener Compositions Comprising High Fructose Corn Syrup A) Perkasil® SM 660 (1.5 gram), is added in portions to 26.8 gram High Fructose Corn Syrup Isoglucose F42 (70% total sugar by weight; 42% fructose/58% glucose, dry solid wt/wt) while stirring to produce a ratio of 8% silica to total sugar content (wt/wt). The clear yellow dispersion is sonicated for 30 min at 40° C. The mixture is cooled to room temperature to produce the final sweetener composition, 21A.

B) Perkasil® SM 660 (0.9 gram), is added in portions to 27.0 gram High Fructose Corn Syrup Isoglucose F42 (70% total sugar by weight; 42% fructose/58% glucose, dry solid wt/wt) while stirring to produce a ratio of 8% silica to glucose content (wt/wt). The clear yellow dispersion is sonicated for 30 min at 40° C. The mixture is cooled to room temperature to produce the final sweetener composition, 21B.

C) Perkasil® SM 660 (1.5 gram), is added in portions to 26.1 gram High Fructose Corn Syrup Isoglucose F50 (72% total sugar by weight; 50% fructose, 47% glucose dry solid, wt/wt) while stirring to produce a ratio of 8% silica to total sugar content (wt/wt). The clear yellow dispersion is sonicated for 30 min at 40° C. The mixture is cooled to room temperature to produce the final sweetener composition, 21C.

D) Perkasil® SM 660 (0.7 gram), is added in portions to 26.0 gram High Fructose Corn Syrup Isoglucose F50 (72% total sugar by weight; 50% fructose, 47% glucose dry solid, wt/wt) while stirring to produce a ratio of 8% silica to glucose content (wt/wt). The clear yellow dispersion is sonicated for 30 min at 40° C. The mixture is cooled to room temperature to produce the final sweetener composition, 21D.

Example 22: Taste Test of Sweetener Compositions Comprising High Fructose Corn Syrup Each taster is given each sample twice (7 mg) of each of the following 6 sweetener compositions sequentially: Isoglucose F42 (Galam), 21A, 21B, Isoglucose F50 (Galam), 21C, 21D, and records their observations after each test. The observations are recorded in the following table:

| | Isoglucose F42 | 21A | 21B | Isoglucose F50 | 21C | 21D |
|---|---|---|---|---|---|---|
| Taster 1 | X | X + 1 | X + 2 | Y | Y + 1 | Y + 1 |
| Taster 2 | X | X + 1.5 | X+ | Y Sweeter than F42 | Y + 1 | Y + 1 |
| Taster 3 | X | X + 1 | X | Y Sweeter than F42 | Y | Y + 0.5 |
| Taster 4 | X | X + 1.5 | X + 1.5 | Y | Y | Y + 1.5 |
| Taster 5 | X | X + 1 | X + 1 | Y | Y + 1 | Y + 1 |

Key:
X represents a level of sweetness,
X + 0.5 represents a taste that is sweeter than X,
X + 1 represents a taste that is sweeter than X + 0.5,
X + 1.5 represents a lasle that is sweeter than X + 1,
X + 2 represents a taste that is more sweet than X + 1.5.
Y represents a level of sweetness,
Y + 0.5 represents a taste that is more sweet than Y,
Y + 1 represents a taste that is more sweet than Y + 0.5,
Y + 1.5 represents a taste that is more sweet than Y + 1.

Example 23: Formation of Hard Candy Comprising Enhanced Sweetener Compositions 154.023 g of High Fructose Corn Syrup (HFCS) Isoglucose F42 is added to 98 g of sucrose and mixed in a pot over medium heat until the sucrose completely dissolves. 60 g of water is added, and the solution is stirred with a whisk. The liquid is heated to a temperature of 149° C. Immediately afterwards it is poured into a mold and cooled at room temperature to produce the final hard candy, 23A.

92.406 g of HFCS+S1 (Isoglucose F42 with 8% Perkasil to glucose content (wt/wt)) is added to 60 g of water and mixed in a pot over medium heat. 98 g of sucrose is added, and the solution is stirred with a whisk. The liquid is heated to a temperature of 149° C. Immediately afterwards it is poured into a mold and cooled at room temperature to produce the final hard candy, 23B.

154.015 g of HFCS Isoglucose F42 is added to 60 g of water and mixed in a pot over medium heat. 58.80 g of the S1 composition is added, and the solution is stirred with a whisk. The liquid is heated to a temperature of 149° C. Afterwards it is poured into a mold and cooled at room temperature to produce the final hard candy, 23C.

Example 24: Taste Test of Hard Candy Comprising Enhanced Sweetener Compositions Each taster is given each of the following 4 hard candies and records their observations after each test. The observations are recorded in the following table:

| Taster | 23A | 23B | 23C |
| --- | --- | --- | --- |
| Taster 1 | X | X + 1 | X + 2 |
| Taster 2 | X | X + 1 Different sweetness, longer sweet taste. | X + 1 Caramel notes |
| Taster 3 | X | X + 1 Late sweetness. | X + 2 |

Example 25: Formation of Meringue Comprising Enhanced Sweetener Compositions Oven is preheated to 93.3° C. (200° F.). A pinch of the S1 composition is added to the egg whites (97 g) before whipping. The egg whites are whipped on a low setting in a stainless steel or ceramic bowl. The remaining S1 composition (82.5 g for 50% sugar reduction, 99 g for 40% sugar reduction) is divided into five equal portions. After about a minute of whipping, the egg whites become foamy and one portion of the S1 composition is added slowly to the egg whites. After about 1.5-2 minutes, the egg whites expand in volume by two to three-fold and another portion of the S1 composition is added slowly. In 1.5 minute increments, the remaining portions of S1 composition are added slowly. The meringue is whipped until a stiff peak consistency is reached. The meringue is then transferred to a piping bag and is piped into a non-stick pan that can be lined with silicone or parchment paper. The meringue is baked for 3 hours, with the pan rotated every hour. For the control meringue, 165 g of sucrose is used in place of the S1 composition.

Example 26: Taste Test of Meringue Comprising Enhanced Sweetener Compositions 5 trained and experienced panelists assess the meringue samples from Example 25 in a round table discussion tasting format. The sugar Control is assessed and a reference score (using the 0-100 intensity scale) for Overall Sweetness is discussed and agreed to. Sugar Reduction samples containing S1 composition are then tasted and consensus scores are agreed upon for overall sweetness. Notes are also made on other appearance, aroma, flavor, texture, and aftertaste attributes of each sample. Individual overall sweetness intensity ratings for all samples (coded) are then carried out in sensory booths, in duplicate, using the 0-100 line scale. Analysis of data is carried out to establish if there are any differences between the sugar control and each of the Sugar Reduction formulations for Overall Sweetness.

Tasting of Control:
Not very much immediate sweetness but then grew. Overall sweetness agreed as about 55 on 0-100 point scale. Some additional slight flavors of malt and egg white. Moderately high initial bite and fast rate of breakdown in texture. Sweetness and some bitterness in aftertaste.

Tasting of 50% Sugar Reduction Sample:
Sweetness close to Control. Some barley sugar flavor and chalky flavor. Some chalkiness in texture.

Tasting of 40% Sugar Reduction Sample:
Sweeter than control. Slight chalkiness but much less than 50% Sugar Reduction Sample.

Overall sweetness rating scores on a 0-100 intensity scale for 5 panelists in duplicate tastings are shown.

| Sample | Overall Sweetness |
| --- | --- |
| Control | 52.2 |
| 50% Sugar Reduction | 53.9 |
| 40% Sugar Reduction | 70.5 |

Example 27: Formation of Whipped Cream Comprising Enhanced Sweetener Compositions Double cream (223 g, Sainsbury) is used for preparing the samples. The S1 composition (13.83 g for 35% sugar reduction, 14.9 g for 30% sugar reduction) is added gradually after two minutes of whipping the cream, while the hand mixer (low setting) whipped the cream to the desired consistency. For the control whipped cream, sucrose (21.28 g) is used in place of the S1 composition. For the Stevia whipped cream, Stevia extract (0.1059 g) is used in place of the S1 composition.

Example 28: Taste Test of Whipped Cream Comprising Enhanced Sweetener Compositions Control, 35% Sugar Reduction, 30% Sugar Reduction, and Stevia whipped cream samples are evaluated using Descriptive Sensory Profiling with a panel of eleven trained assessors. Two 2 hr discussion and training sessions are held. During these sessions, the panel evaluates all products and developed and agrees to a descriptive vocabulary covering appearance, aroma, flavor, texture, mouthfeel, and aftertaste characteristics of the samples. Assessors carry out formal attribute intensity rating of all samples, working alone in individual sensory evaluation booths. Ratings are made using a 100 point unstructured line scale, with verbal anchors, from low to high. Each sample is presented to the assessors labeled with a three digit code and is evaluated three times by each assessor during a 2.5 hr session. Samples are presented according to a balanced design. Evaluations are made in mouth, immediately after swallowing, one minute after swallowing, and two minutes after swallowing for key residual after effects. Plain crackers and mineral water are used as palate cleansers between samples. All samples are assessed in tasting booths designed to ISO 8589:2007, illuminated with Northern daylight. As part of the training, the panel agrees to a reference score of 80 for the overall sweetness of the whipped double cream control sample. The reduced sugar samples containing the S1 composition are then compared to the control. The sample order is randomized to avoid potential bias. Data for each attribute is analyzed using analysis of variance to identify attributes that discriminate samples at the 5% level of significance (P<0.05).

Whipped Double Cream: Appearance and Aroma

| Attributes | 35% Sugar Reduction | | 30% Sugar Reduction | | Control | | Stevia | |
|---|---|---|---|---|---|---|---|---|
| Number of Surface Holes Appearance | 21.1 | a | 21.4 | a | 22.8 | a | 22.3 | a |
| Size of Surface Holes Appearance | 17.6 | a | 17.6 | a | 21.6 | a | 16.7 | a |
| Depth of Color Appearance* | 65.1 | a | 61.7 | ab | 59.6 | b | 59.8 | b |
| Whipped Appearance | 63.7 | a | 64.2 | a | 64.5 | a | 60.3 | a |
| Overall Aroma | 22.6 | a | 20.5 | a | 24.4 | a | 21.9 | a |
| Creamy Aroma* | 23.0 | ab | 18.8 | b | 25.6 | a | 19.4 | ab |
| Cooked Sugar Aroma | 3.0 | a | 3.9 | a | 4.2 | a | 1.6 | a |

*Indicates a significant difference at the 95% confidence level.
Where samples share the same letter, there is no significant difference at the 95% confidence level All samples are very similar in appearance. Only the 35% Sugar Reduction sample is significantly creamier in color compared to the Control and Stevia samples. All samples have a similar creamy aroma. Only the 35% Sugar Reduction sample is significantly lower compared to the Control. All other samples are comparable.

Whipped Double Cream: Flavor in Mouth

| Attributes | 35% Sugar Reduction | | 30% Sugar Reduction | | Control | | Stevia | |
|---|---|---|---|---|---|---|---|---|
| Sweetness Onset Flavor* | 10.8 | b | 12.9 | ab | 10.5 | b | 15.7 | a |
| Sweetness Build Flavor* | 28.0 | b | 30.7 | b | 31.3 | b | 46.8 | a |
| Overall Sweetness Flavor | 57.4 | a | 58.5 | a | 65.5 | a | 60.4 | a |
| Bitter Flavor* | 2.1 | b | 3.3 | b | 0.2 | b | 30.8 | a |
| Creamy Flavor* | 51.6 | a | 50.7 | a | 53.9 | a | 40.8 | b |
| Liquorice Flavor* | 0.2 | b | 0.1 | b | 0.3 | b | 67.5 | a |
| Metallic Flavor* | 1.6 | b | 4.8 | b | 0.7 | b | 23.3 | a |

*Indicates a significant difference at the 95% confidence level.
Where samples share the same letter, there is no significant difference at the 95% confidence level Both Sugar Reduction samples are deemed to be equivalently sweet to the Control and Stevia samples while in the mouth. Sugar reduction samples are also at parity with the Control for Sweetness Onset and Build. There are no significant differences in any other flavor attributes between the Sugar Reduction samples and the Control. However, the Stevia sample imparts far more detrimental flavors, the Sweetness takes longer to build compared to all other samples, and the sample is less Creamy and far more Bitter and Metallic tasting. The Stevia sample also has a strong Liquorice flavor, which is absent in all other samples.

Whipped Double Cream: Texture and Mouthfeel in Mouth

| Attributes | 35% Sugar Reduction | | 30% Sugar Reduction | | Control | | Stevia | |
|---|---|---|---|---|---|---|---|---|
| Smooth Texture | 70.3 | a | 71.2 | a | 73.4 | a | 73.4 | a |
| Soft Texture | 73.5 | a | 74.6 | a | 74.8 | a | 75.0 | a |
| Density Texture | 51.4 | a | 52.7 | a | 49.5 | a | 51.1 | a |
| Rate of Melt Texture* | 26.7 | b | 30.2 | ab | 26.3 | b | 32.1 | a |
| Oily Mouth Coating Mouthfeel | 25.7 | a | 29.2 | a | 24.8 | a | 28.7 | a |
| Salivating Mouthfeel* | 37.2 | b | 34.2 | b | 39.9 | ab | 45.0 | a |
| Mouth Drying Mouthfeel | 27.8 | a | 31.4 | a | 27.3 | a | 34.8 | a |

*Indicates a significant difference at the 95% confidence level.
Where samples share the same letter, there is no significant difference at the 95% confidence level There are no significant textural or mouthfeel differences between the Sugar Reduction and Control samples. The Stevia sample melts more quickly and is more Salivating compared to the 35% Sugar Reduction and Control samples. All samples are very soft and smooth with a middling firm density. A low oily mouth coating could be felt while the samples are broken down in the mouth, and all are comparably mouth drying at a low to moderate level.

Whipped Double Cream: Immediate Aftertaste

| Attributes | 35% Sugar Reduction | | 30% Sugar Reduction | | Control | | Stevia | |
|---|---|---|---|---|---|---|---|---|
| Overall Sweetness Aftertaste* | 46.9 | b | 50.7 | ab | 56.5 | a | 52.3 | ab |
| Bitter Aftertaste* | 4.5 | b | 4.3 | b | 2.1 | b | 34.9 | a |
| Creamy Aftertaste* | 44.8 | a | 46.1 | a | 47.0 | a | 36.0 | b |
| Liquorice Aftertaste* | 0.2 | b | 0.2 | b | 0.1 | b | 59.2 | a |
| Metallic Aftertaste* | 5.2 | b | 6.7 | b | 5.6 | b | 27.5 | a |
| Oily Mouth Coating Aftereffect | 25.8 | a | 27.5 | a | 24.3 | a | 23.9 | a |
| Salivating Aftereffect | 38.7 | a | 38.5 | a | 41.2 | a | 41.9 | a |
| Mouth Drying Aftereffect* | 38.1 | b | 40.4 | b | 38.6 | b | 49.1 | a |

*Indicates a significant difference at the 95% confidence level.
Where samples share the same letter, there is no significant difference at the 95% confidence level The 30% Sugar Reduction sample is at parity with the Control and Stevia samples for Overall Sweetness in Immediate Aftertaste. The 35% Sugar Reduction sample is significantly less sweet compared to Control at this stage, however by 1 minute it is equivalently sweet compared to the Control once again. The Stevia sample remains significantly more Bitter, Metallic, and Liquoricy tasting compared to the other samples. All samples leave a similarly low oily coating in the mouth and are moderately salivating. The Stevia sample is significantly more Mouth Drying compared to the rest of the samples.

Whipped Double Cream: Aftertaste at 1 Minute

| Attributes | 35% Sugar Reduction | | 30% Sugar Reduction | | Control | | Stevia | |
|---|---|---|---|---|---|---|---|---|
| Overall Sweetness Aftertaste | 41.0 | a | 41.1 | a | 47.5 | a | 45.9 | a |
| Bitter Aftertaste* | 6.1 | b | 3.7 | b | 3.9 | b | 31.5 | a |
| Creamy Aftertaste* | 38.3 | a | 37.3 | ab | 38.1 | a | 29.5 | b |
| Liquorice Aftertaste* | 0.1 | b | 0.2 | b | 0.2 | b | 51.6 | a |
| Metallic Aftertaste* | 8.0 | b | 7.7 | b | 5.2 | b | 29.0 | a |
| Oily Mouth Coating Aftereffect | 21.9 | a | 25.3 | a | 21.7 | a | 22.7 | a |
| Salivating Aftereffect* | 31.3 | ab | 29.6 | b | 36.3 | ab | 37.6 | a |
| Mouth Drying Aftereffect* | 47.3 | ab | 48.1 | ab | 42.5 | b | 51.5 | a |

*Indicates a significant difference at the 95% confidence level.
Where samples share the same letter, there is no significant difference at the 95% confidence level 1 Minute after Swallowing all samples are equivalently sweet overall. The Stevia sample remains significantly more Bitter, Metallic, and Liquorice tasting compared to the other samples. All samples leave a similarly low oily coating in the mouth and are moderately salivating. The Stevia sample is significantly more Mouth Drying compared to the rest of the samples.

Whipped Double Cream: Aftertaste at 2 Minutes

| Attributes | 35% Sugar Reduction | | 30% Sugar Reduction | | Control | | Stevia | |
| --- | --- | --- | --- | --- | --- | --- | --- | --- |
| Liquorice Aftertaste* | 0.4 | b | 0.2 | b | 0.2 | b | 47.1 | a |
| Tingling Aftereffect | 11.0 | a | 13.6 | a | 10.3 | a | 14.8 | a |
| Numbing Aftereffect | 18.6 | a | 22.0 | a | 20.3 | a | 19.7 | a |
| Mouth Drying Aftereffect | 48.4 | a | 49.0 | a | 46.5 | a | 51.0 | a |

*Indicates a significant difference at the 95% confidence level.
Where samples share the same letter, there is no significant difference at the 95% confidence level Even 2 minutes after swallowing, the Stevia sample continues to impart significantly stronger Liquorice flavors at a moderate intensity. By 2 minutes, all samples are at parity for after effects; both Numbering and Tingling are felt at low levels. Mouth Drying persists in all samples at a comparably moderate level.

Overall Sweet Flavor intensity as a function of time for whipped double cream samples is shown in FIG. 1. Although the control is numerically slightly sweeter at all time points, the differences for the most part are very small and are not statistically significant. All samples starts off moderately high in Sweet intensity. Although there is a drop in sweet flavor in all, samples retain a moderate sweet aftertaste by 1 minute. Immediately after swallowing the 35% Sugar Reduction sample is significantly less sweet compared to the Control; by 1 minute it is at parity with the Control once more. There is no significant difference in Overall Sweetness between the 35% and 30% Sugar Reduction samples containing the S1 composition.

Figure 2:
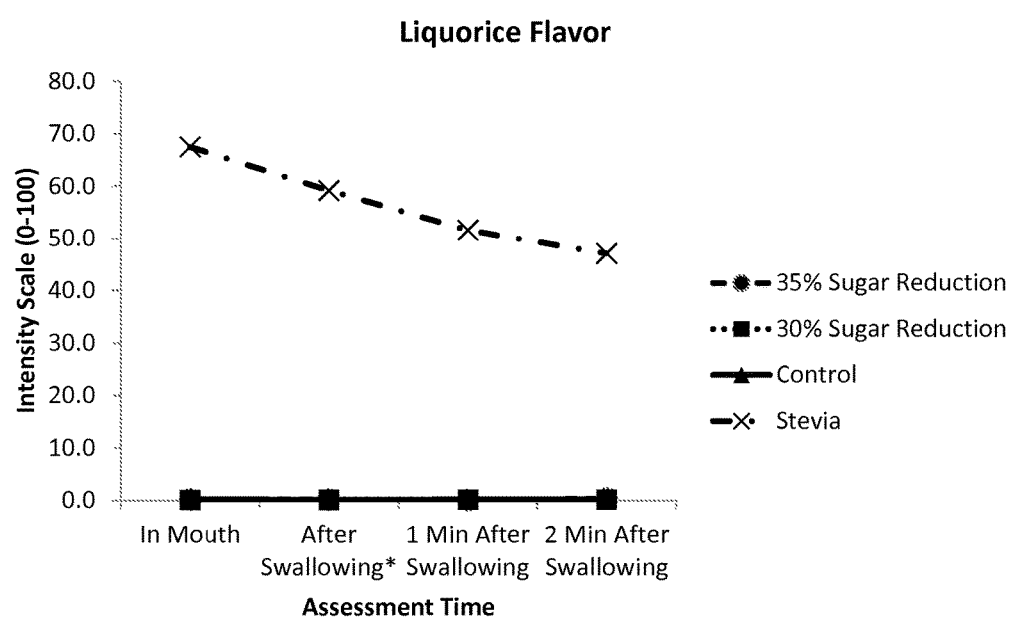
FIG. 2 shows liquorice flavor intensity as a function of time for whipped double cream samples.

Liquorice Flavor intensity as a function of time for whipped double cream samples is shown in FIG. 2. The Liquorice flavor is a unique and detrimentally perceived characteristic of the Stevia sample that makes it stand out from the rest of the samples being profiled. The flavor is significantly stronger in the Stevia sample for the duration of the rating. The flavor starts off strong in the mouth and reduces over time leaving a moderately intense aftertaste by 2 minutes.

Figure 3:
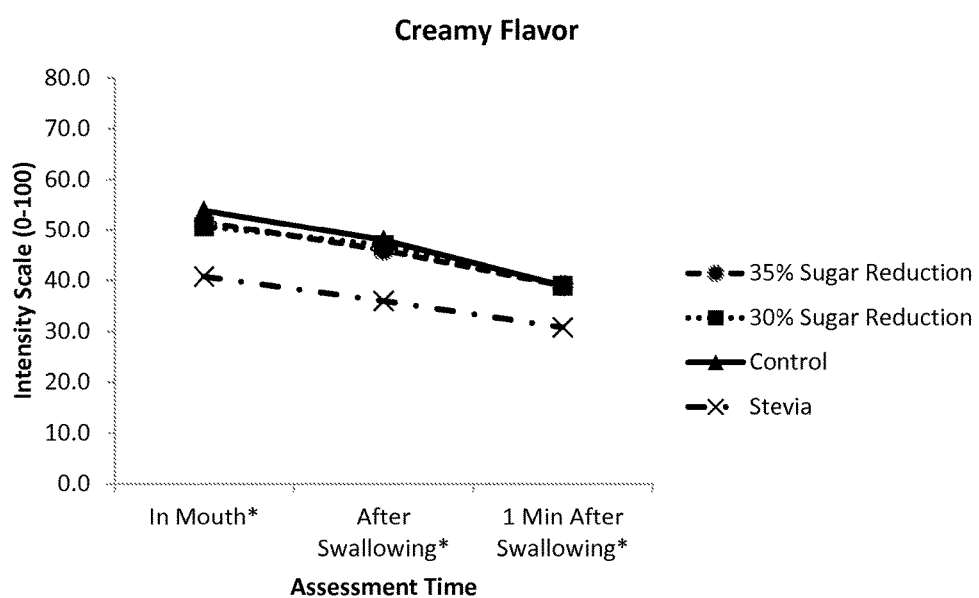
FIG. 3 shows creamy flavor intensity as a function of time for whipped double cream samples.

Creamy Flavor intensity as a function of time for whipped double cream samples is shown in FIG. 3. The Reduced Sugar samples and Control are comparably creamy at all time points. All three are significantly higher compared to the Stevia sample.

Figure 4:
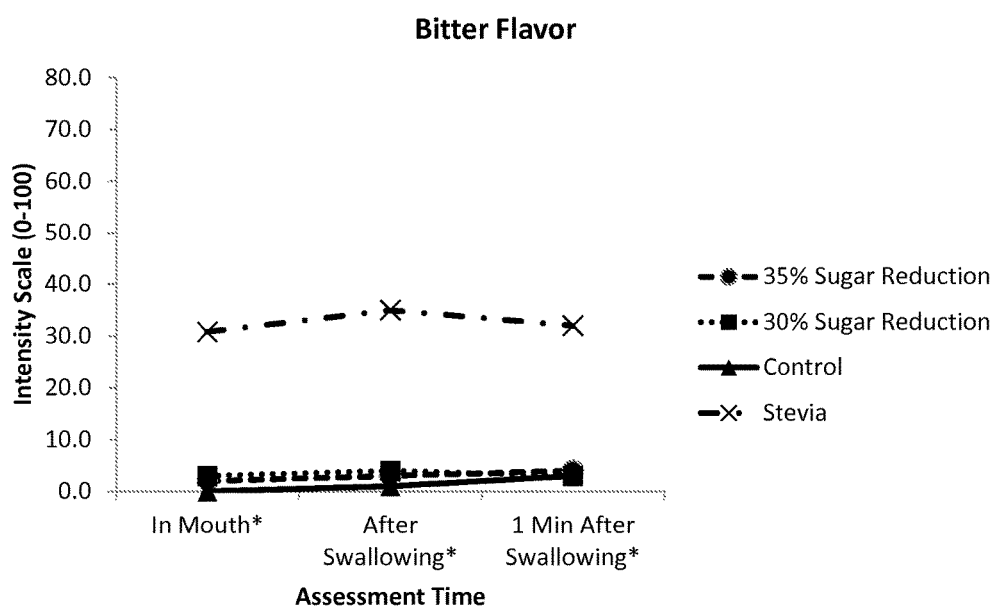
FIG. 4 shows bitter flavor intensity as a function of time for whipped double cream samples.

Bitter Flavor intensity as a function of time for whipped double cream samples is shown in FIG. 4. Bitterness is not a key flavor feature in the Control or Sugar Reduced samples containing the S1 composition. Bitterness remains significantly higher, at a low-moderate intensity, in the Stevia sample compared to the rest of the sample set.

Figure 5:
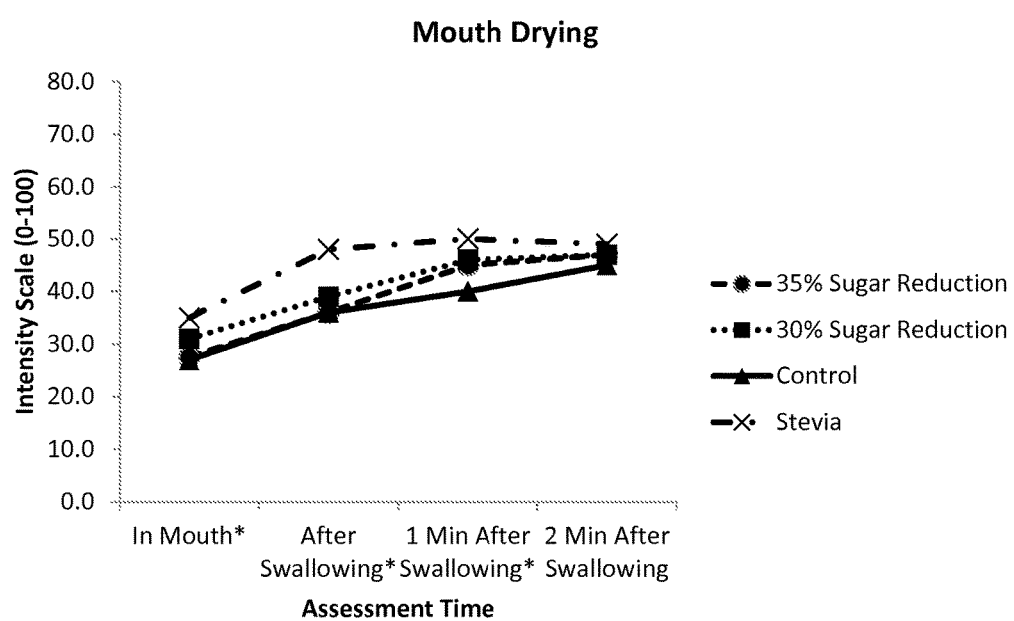
FIG. 5 shows mouth drying intensity as a function of time for whipped double cream samples.

Mouth Drying intensity as a function of time for whipped double cream samples is shown in FIG. 5. Mouth Drying is perceived at a similarly low level in all samples while the whipped double cream is in mouth. Mouth Drying increases for all samples once swallowed, significantly more so in the Stevia sample compared to the other samples. Drying continues to increase by 1 minute, however the Stevia sample is only significantly more drying compared to the Control. The 35% and 30% Reduced Sugar samples are at parity with both the Stevia sample and the Control, and by 2 minutes all samples peak, leaving similarly moderate levels of Mouth Drying.

Overall the Sugar Reduction samples containing the S1 composition offer a very similar sensory profile compared to the Control for all modalities. Both Sugar Reductions containing the S1 composition are equivalently sweet compared to the Control and Stevia sample while in the mouth and 1 minute after swallowing. The 35% Sugar Reduction sample is significantly less sweet compared to the Control immediately after the cream is swallowed. The 35% and 30% Sugar Reduction whipped creams are no more mouth drying than the Control. The Stevia sample stands out due to its unique, intense, and residual liquorice flavor and its detrimental metallic and bitter flavors which are significantly stronger compared to the other samples. These notes clearly mask the creamy flavor, which is significantly lower compared to the other samples.

The present invention may be embodied in other specific forms without departing from the spirit or essential attributes thereof.

What is claimed is:

1. A method of making a sweetener composition, the method comprising:
   mixing a carrier compound with a syrup to form a substantially uniform dispersion, wherein the syrup comprises a solvent and one or more sweetener carbohydrates; and
   sonicating the dispersion to associate the one or more sweetener carbohydrates with the carrier compound to form a sweetener composition, wherein the sweetener composition comprises at least 20% by weight water, and from 10% to 70% by combined weight of the carrier compound and the one or more sweetener carbohydrates;
   wherein the sweetener composition is in a syrup form and has enhanced sweetness compared to a control composition; and wherein the control composition consists of the same contents by identity and quantity as the sweetener composition but without the carrier compound.

2. The method of claim 1, further comprising mixing the solvent with the one or more sweetener carbohydrates to form the syrup.

3. The method of claim 1, further comprising drying the sweetener composition.

4. The method of claim 1, further comprising passing the sweetener composition through a sieve or sieving tower.

5. The method of claim 1, wherein the sweetener composition comprises up to 12% carrier compound weight/weight relative to a sum of total sweetener carbohydrate and sweetener polyol.

6. The method of claim 5, wherein the sweetener composition comprises 8-10% carrier compound weight/weight relative to a sum of total sweetener carbohydrate.

7. The method of claim 1, wherein the sweetener composition comprises up to 8% carrier compound weight/weight relative to a sum of total sweetener carbohydrate.

8. The method of claim 1, wherein the solvent is water.

9. The method of claim 1, wherein the syrup has a ratio of total sweetener carbohydrate to water of at least 55:45.

10. The method of claim 1, wherein the syrup has a ratio of total sweetener carbohydrate to water of at least 60:40.

11. The method of claim 1, wherein the syrup has a ratio of total sweetener carbohydrate to water of at least 65:35.

12. The method of claim 1, wherein the carrier compound is selected from the group consisting of silica, chitosan, chitin, starch, maltodextrin, microcrystalline cellulose, hemicellulose, a cyclodextrin, a hydroxyalkyl cyclodextrin, inulin, pectin, a carrageenan, titanium dioxide, magnesium oxide, magnesium hydroxide, calcium oxide, calcium carbonate, and a natural gum.

13. The method of claim 1, wherein the carrier compound is chitosan.

14. The method of claim 1, wherein the carrier compound is silica.

15. The method of claim 14, wherein the silica is precipitated silica.

16. The method of claim 14, wherein the silica is silica gel.

17. The method of claim 14, wherein the carrier compound has an average particle size of at least 1 micron and of up to 60 microns and a specific surface area of at least 60 $m^2/g$.

18. The method of claim 1, wherein the one or more sweetener carbohydrates are sucrose, glucose, maltose, lactose, high fructose corn syrup, high maltose corn syrup, or a combination thereof.

19. The method of claim 1, wherein the sweetness is enhanced by at least 10%.

\* \* \* \* \*